US011881119B2

(12) United States Patent
Eckert et al.

(10) Patent No.: US 11,881,119 B2
(45) Date of Patent: Jan. 23, 2024

(54) MODELING AIR LEAKS IN LUNGS

(71) Applicant: Ethicon LLC, Guaynabo, PR (US)

(72) Inventors: Chad E. Eckert, Milford, OH (US);
Jordan B. Wong, Cincinnati, OH (US);
Charles C. Klassen, Boston, MA (US);
Harald C. Ott, Wenham, MA (US);
Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 1132 days.

(21) Appl. No.: 16/196,910

(22) Filed: Nov. 20, 2018

(65) Prior Publication Data

US 2019/0172371 A1 Jun. 6, 2019

Related U.S. Application Data

(60) Provisional application No. 62/595,284, filed on Dec. 6, 2017.

(51) Int. Cl.
*G09B 23/28* (2006.01)
*G09B 23/32* (2006.01)
(Continued)

(52) U.S. Cl.
CPC ......... *G09B 23/288* (2013.01); *G09B 23/303* (2013.01); *G09B 23/306* (2013.01); *G09B 23/32* (2013.01); *A61B 5/08* (2013.01)

(58) Field of Classification Search
CPC .................................................. G09B 23/288
(Continued)

(56) References Cited

U.S. PATENT DOCUMENTS 4,167,070 A * 9/1979 Orden .................... G09B 23/32
434/272
4,542,643 A 9/1985 Himmelstein
(Continued)

FOREIGN PATENT DOCUMENTS

CN 101977649 A 2/2011
CN 101983324 A 3/2011
(Continued)

OTHER PUBLICATIONS

Abolhoda, A., Liu, D., Brooks, A. & Burt, M. "Prolonged air leak following radical upper lobectomy: an analysis of incidence and possible risk factors," Chest, vol. 113, pp. 1507-1510, Jun. 1998.
(Continued)

*Primary Examiner* — Kesha Frisby
(74) *Attorney, Agent, or Firm* — Mintz Levin Cohn Ferris Glovsky and Popeo, P.C.

(57) ABSTRACT

In general, systems, methods, and devices for modeling air leaks in lungs are provided. In an exemplary embodiment, the systems, methods, and devices provide a model to allow for simulation of negative and positive pressure ventilation modes in vitro, which may allow for evaluation and investigation of pathologies and interventions. In addition to ventilation functions the model includes submersion of the lung sample in fluid inside a chamber and cycling the fluid through a collection system to collect air leaked from the lung. The model can allow for quantification and visual observation of air leaks in real time.

20 Claims, 20 Drawing Sheets

(51) Int. Cl.
G09B 23/30 (2006.01)
A61B 5/08 (2006.01)

(58) Field of Classification Search
USPC .......................................................... 434/267
See application file for complete search history.

(56) References Cited

U.S. PATENT DOCUMENTS

| | | | |
|---|---|---|---|
| 6,874,501 | B1 | 4/2005 | Estetter et al. |
| 8,910,509 | B2* | 12/2014 | Terentiev .............. G01M 3/227 73/49.3 |
| 2005/0137714 | A1 | 6/2005 | Gonzalez et al. |
| 2006/0107731 | A1 | 5/2006 | Thomas |
| 2011/0040359 | A1* | 2/2011 | Harris ............... A61M 16/0666 607/105 |
| 2012/0150057 | A1* | 6/2012 | Mantri ................... A61B 5/091 600/538 |
| 2013/0177972 | A1* | 7/2013 | Green .................. G06K 19/067 235/487 |
| 2017/0292214 | A1* | 10/2017 | Scharf ..................... D06F 19/00 |
| 2017/0294146 | A1* | 10/2017 | Grubbs .................... G09B 9/00 |

FOREIGN PATENT DOCUMENTS

| | | |
|---|---|---|
| WO | 2017087366 A1 | 5/2017 |
| WO | 2017160228 A1 | 9/2017 |

OTHER PUBLICATIONS

Adler A, Guardo R, "Electrical impedance tomography: Regularized imaging and contrast detection," IEEE Transactions on Medical Imaging, vol. 15, pp. 170-179, 1996.

Aigner, C., et al. "Clinical ex vivo lung perfusion—pushing the limits." Am J Transplant, vol. 12, pp. 1839-1847, Jul. 2012.

Borges JB, Suarez-Sipmann F, Bohm SH, et al. "Regional lung perfusion estimated by electrical impedance tomography in a piglet model of lung collapse," Journal of Applied Physiology, vol. 112, pp. 225-236, Jan. 2012.

Brown B, "Electrical impedance tomography (EIT): A review," Journal of Medical Engineering & Technology, vol. 27, pp. 97-108, 2003.

Brunelli, A. et al. "Air leaks after lobectomy increase the risk of empyema but not of cardiopulmonary complications: a case-matched analysis," Chest, vol. 130, pp. 1150-1156, Jul. 2006.

Cairo, J.M. in Pilbeam's Mechanical Ventilation, Physiological and Clinical Applications, 6th Edition, St. Louis: Elsevier, 2016, p. 1-15.

Cerfolio, R. J., Bass, C. & Katholi, C. R. "Prospective randomized trial compares suction versus water seal for air leaks," Ann Thorac Surg, vol. 71, pp. 1613-1617, May 2001.

Cerfolio, R. J., Bass, C. S., Pask, A. H. & Katholi, C. R. "Predictors and treatment of persistent air leaks," Ann Thorac Surg, vol. 73, pp. 1727-1721, Jun. 2002.

Chae E.J. et al. "Xenon Ventilation CT with a Dual-Energy Technique of Dual-Source CT: Initial Experience," Radiology, vol. 248, pp. 615-624, 2008.

Charest J.M., et al. "Design and validation of a clinical-scale bioreactor for long-term isolated lung culture," Biomaterials, vol. 52:pp. 79-87, Jun. 2015.

Curtis CG, Bilyard K, Stephenson H. "Ex Vivo MetricsTM, a preclinical tool in new drug development," Journal of Translational Medicine, Jan. 2008.

Cypel, M., et al. "Normothermic Ex Vivo Lung Perfusion in Clinical Lung Transplantation," New England Journal of Medicine, vol. 364, pp. 1431-1440, Apr. 2011.

De Lange E.E., et al. "The Variaibility of Regional Airflow Obstruction within the Lungs of Patients with Asthma: Assessment with Hyperpolarized Helium-3 Magnetic Resonance Imaging," J Allergy Clin Immunol, vol. 119, pp. 1072-1078, May 2007.

Driehuys B. et al. "Imaging Alveolar-Capillary Gas Transfer Using Hyperpolarized 129Xe MRI," PNAS, vol. 103, pp. 18278-18283, Oct. 2006.

Elsayed, H., McShane, J. & Shackcloth, M. "Air leaks following pulmonary resection for lung cancer: is it a patient or surgeon related problem?" Ann R Coll Surg Engl, vol. 94, pp. 422-427, Sep. 2012.

Frerichs I, Hinz J, Herrmann p et al. "Regional lung perfusion as determined by electrical impedance tomography in comparison with electron beam CT imaging," IEEE Transactions on Medical Imaging, vol. 21, pp. 646-652, Jun. 2002.

Holder, D, "Clinical and physiological applications of electrical Impedance tomography," Thorax,. pp. 626-626, Jun. 1994.

Jung J-W, et al al. "New Insights into the Assessment of Asthma Using Xenon Ventilation Computed Tomography," Ann Allergy Asthma Immunol, vol. 111, pp. 90-95, 2013.

Koike T, Yeung JC, Cypel M, Rubacha M, Matsuda Y, Sato M, et al. "Kinetics of lactate metabolism during acellular normothermic ex vivo lung perfusion," J Heart Lung Transplant, vol. 30, pp. 1312-1319, Sep. 2011.

Kunst PWA, Noordegraaf AV, Hoekstra OS, Postmus PE, Vries PMJM de., "Ventilation and perfusion imaging by electrical impedance tomography: A comparison with radionuclide scanning," Physiological Measurement, vol. 19, pp. 481-490, 1998.

Linder, A., et al. "The Ex-Vivo Isolated, Perfused Human Lung Model: Description and Potential Applications." Thorac Cardiovasc Surg, vol. 44, pp. 140-146, 1996.

Macchiarini, P., et al. "Ex vivo lung model of pig-to-human hyperacute xenograft rejection." J Thorac Cardiovasc Surg, vol. 114, pp. 315-325, Sep. 1997.

Miller, M. R., et al. "Standardisation of spirometry," Eur Respir J, vol. 26, pp. 319-338, 2005.

Nelson K, Bobba C, Eren E, et al. Method of Isolated Ex Vivo Lung Perfusion in a Rat Model: Lessons Learned from Developing a Rat EVLP Program. Journal of Visualized Experiments, vol. 96, Feb. 2015.

Nelson K, Bobba C, Ghadiali S, Jr DH, Black SM, Whitson BA, "Animal models of ex vivo lung perfusion as a platform for transplantation research," World Journal of Experimental Medicine, vol. 4, pp. 7-15, May 2014.

Nguyen DT, Kosobrodov R, Barry MA, et al. "Preliminary results on different Impedance contrast agents for pulmonary perfusion imaging with electrical Impedance tomography," Journal of Physics: Conference Series, vol. 21, pp. 434, 2013.

Niemeier, R. W. "The isolated perfused lung," Environmental Health Perspectives, vol. 56, pp. 35-41, Jun. 1984.

Okada, S., Shimada, J., Kato, D., Tsunezuka, H. & Inoue, M. "Prolonged air leak following lobectomy can be predicted in lung cancer patients," Surg Today, vol. 47, pp. 973-979, Aug. 2017.

Ott, H. C., et al. "Regeneration and orthotopic transplantation of a bioartificial lung," Nat Med, vol. 16, pp. 927-933, 2010, Available: http://www.nature.com/nm/journal/v16/n8/full/nm.2193.html?foxtrotcallback=true.

Padilla A.M. and Padilla J.D. "Lung Preservation: Current Practices," Arch Bronconeumol, vol. 40, pp. 86-93, Feb. 2004.

Petersen TH, Calle EA, Colehour MB, Niklason LE, "Bioreactor for the long-term culture of lung tissue," Cell Transplantation, vol. 20, pp. 1117-1126, 2011.

Pierce, R, "Spirometry: an essential clinical measurement," Australian Family Physician, vol. 34, No. 7, pp. 535-539, Jul. 2005.

Ren, X., et al. "Engineering pulmonary vasculature in decellularized rat and human lungs." Nat Biotech vol. 33: pp. 1097-1102, Oct. 2015.

Rusch, V. W., Capps, J. S., Tyler, M. L. & Pierson, D. L. "The performance of four pleural drainage systems in an animal model of bronchopleural fistula," Chest, vol. 93, pp. 859-863, Apr. 1988.

Singhal, S. et al. "Management of alveolar air leaks after pulmonary resection," Ann Thorac Surg, vol. 89, pp. 1327-1335, Jun. 2010.

Steen, S., et al. "First human transplantation of a nonacceptable donor lung after reconditioning ex vivo," Ann Thorac Surg, vol. 83, pp. 2191-2194, Jun. 2007.

(56) References Cited

OTHER PUBLICATIONS

Varela, G., Jimenez, M. F., Novoa, N. & Aranda, J. L. "Estimating hospital costs attributable to prolonged air leak in pulmonary lobectomy," Eur J Cardiothorac Surg, vol. 27, pp. 329-333, Feb. 2005.

Wang, L. S., et al. "The effect of ischemic time and temperature on lung preservation in a simple ex vivo rabbit model used for functional assessment," J Thorac Cardiovasc Surg, vol. 98, pp. 333-342, Sep. 1989.

Y. Mamatjan, P. Gaggero, S. Böhm, A. Adler, "Use of temperature as a contrast agent in electrical impedance tomography," presented at the Canadian Medical and Biological Engineering Society, (CMBEC36), Ottawa, Canada. May 2013.

Yoo, A., et al., "Burden of air leak complications in thoracic surgery estimated using a national hospital billing database," ClinicoEconomics and Outcomes Research, vol. 9, pp. 373-383, 2017.

European Search Report for EP App. No. 18210874.6 dated Mar. 8, 2019 (7 pages).

International Search Report and Written Opinion for Intl. App. No. PCT/IB2018/059665 dated Mar. 8, 2019 (10 pages).

Yeung et al., "Normothermic Ex Vivo Lung Perfusion in Clinical Lung Transplantation," Current Transplantation Reports, vol. 2, No. 4, Oct. 10, 2015, pp. 324-328.

\* cited by examiner

MODELING AIR LEAKS IN LUNGS

CROSS REFERENCE TO RELATED APPLICATIONS

The present application claims priority to U.S. Provisional Patent Application No. 62/595,284 entitled "Ex Vivo Modeling of Perioperative Air Leaks in Porcine Lungs" filed Dec. 6, 2017, which is hereby incorporated by reference in its entirety.

FIELD

The present disclosure relates generally to modeling air leaks in lungs.

BACKGROUND

Prolonged air leaks (PALs) are one of the most common complications after pulmonary resections. Most PALs develop immediately after surgical resection or during the first postoperative day. Several studies have shown that air leaks (in particular PALs) are associated with a variety of postoperative complications, such as increased risk of empyema, atelectasis, pneumonia, and mortality. The Society of Thoracic Surgeons (STS) defines a PAL as an air leak extending the otherwise necessary length of stay. For lobectomy, this can be the fourth, fifth, or sixth postoperative day based on different classifications. Air leaks are associated with increased patient discomfort due to prolonged chest tube drainage and hospitalization and amplified health care costs due to increased use of inpatient and outpatient resources.

Numerous risk factors have been proposed to be associated with air leaks following thoracic surgery. These factors are diverse and include patient gender, presence of adhesions, presence of a pneumothorax or an incomplete fissure, upper lobectomy, performance of an anatomical resection, presence of chronic obstructive pulmonary disease, preoperative use of steroids, fragile or aged lung parenchyma, adhesions requiring mobilization of the lung, body mass index, surgical technique, the experience of the surgeon, chest tube management postoperatively (suction vs water seal), and rupture of pre-existing blebs. Unfortunately, such factors are not fully predictive; additionally, since the standard of care often involves waiting for leaks to resolve, surgeons rarely re-operate to address PALs, thus further limiting knowledge around leak etiology. A deeper understanding of PAL etiology could help drive innovation in the treatment and care of PAL and may ultimately reduce and prevent their occurrence.

To date, surgical and benchtop models have suffered from limitations that hinder progress towards understanding and addressing PALs. Air leaks have been simulated in in vivo and ex vivo models, but studies showing the sources of air leaks, quantifying the volume and/or frequency of leaks, or investigating leaks under physiologically relevant mechanics and disease states are lacking. In vivo models are often restricted to the use of young, healthy animals that are free of disease and are not generally at a high risk for leaks. Though these models closely reflect proper lung mechanics, they do not allow for direct observation of leak sites or quantification of leak rates. Existing ex vivo models permit direct visualization of the leak site and can more easily quantify leak rates, but are often performed under ventilator-assisted breathing which does not have the same ventilation mechanics as physiological breathing. Neither method has been rigorously used to investigate possible stressors leading to air leaks such as cough or physiologic deep breathing.

Given the lower cost, ability to use non-dedicated animal tissue, and ability to directly visualize and quantify leaks, ex vivo isolated lung models offer the possibility of functional and biological testing in a controlled systematic manner. Such isolated lung models have been in use since at least 1989, and more recent iterations have advanced the quantification and control of physiological conditions; however, the goal of replicating physiologic (and more specifically perioperative conditions and various ventilation modalities) has proven to be difficult. Tangentially, ex vivo lung perfusion (EVLP) protocols have been developed as a technique to evaluate and recondition lungs prior to transplantation and may provide an interesting extension to improved ex vivo lung models. During EVLP, lung function is monitored in real time including $dO_2$, $dCO_2$, glucose, and other parameters, which provides quantitative assessment of cellular health and overall tissue function. Despite a high degree of sophistication, current EVLP systems do not attempt to mimic the physiology of the pleural cavity. Instead, the lung is exposed to air and ventilated using positive pressure. Nevertheless, EVLP provides tremendous proof of principle showing that lungs can be ventilated and perfused ex vivo for several hours to observe physiologic function, assess tissue health, and (to a certain extent) repair damage in both porcine and human lungs.

Accordingly, there remains a need for improved modeling of air leaks in lungs.

SUMMARY

In general, systems, methods, and devices for modeling air leaks in lungs are provided.

In one aspect, a medical air leak modeling system is provided that in one embodiment includes a first liquid-tight and air-tight chamber configured to have a liquid therein and to have a lung immersed in the liquid in the first chamber, a second liquid-tight and air-tight chamber, a tube connecting the first chamber with the second chamber to allow liquid to circulate between the first and second chambers, a first pump configured to circulate fluid between the first chamber to the second chamber, a sensor configured to sense a liquid fill level in the second chamber, and a control unit operatively coupled to the sensor. The control unit is configured to, in response to the sensor sensing a threshold amount of change in the fill level, activate a second pump to cause the pump to pump liquid from the first chamber to the second chamber.

The system can vary in any number of ways. For example, fluid can include liquid and air, the second pump can be a peristaltic pump, and the control unit can be configured to use an amount of rotation of the peristaltic pump in pumping the liquid from the first chamber to the second chamber in determining an amount of air moved from the first chamber to the second chamber by the first pump. For another example, the system can include a balloon configured to be immersed in the liquid in the first chamber.

For another example, the system can include a pressure mechanism located outside of the first chamber and configured to inflate and deflate the lung immersed in the liquid in the first chamber. In at least some embodiments, the pressure mechanism can include a ventilator configured to provide oscillating positive pressure to the lung immersed in the liquid in the first chamber and/or a piston configured to provide negative pressure to the lung immersed in the liquid in the first chamber. In at least some embodiments, the system can include a balloon configured to be immersed in the liquid in the first chamber, and the balloon can be configured to deflate from a default inflated state in response to the lung being inflated.

For still another example, a top wall of the first chamber has a dome shape to allow for collection of air between the top wall and a top of the liquid in the first chamber. In at least some embodiments, the system can include a port at a top of the dome shape, the system can include a second tube connected to the port and to the second chamber, the dome shape can be the only domed portion of the top wall, and the first pump can be configured to circulate the fluid through the second tube. In at least some embodiments, the dome shape can include a plurality of dome shapes in the top wall, each of the dome shapes can have a port at a top thereof, and the first pump can be configured circulate the fluid through a selected one of the ports.

For yet another example, the system can include a trachea cannulation port in a wall of the first chamber, and the trachea port can be configured to operatively couple to the lung to allow liquid to flow out of the lung and out of the first chamber through the trachea port. In at least some embodiments, a second tube can extend from the trachea port outside of the first chamber, a pinch valve can be located along the second tube, and the pinch valve can be configured to selectively move between an open position, in which the pinch valve does not obstruct flow through the second tube, and a closed position, in which the pinch valve obstructs flow through the second tube.

For another example, the system can include a heater operatively coupled to the first chamber and configured to heat the lung immersed in the liquid in the first chamber. For yet another example, the control unit can be configured to, in response to the sensor sensing the fill level being substantially equal to a predetermined fill level, deactivate the second pump to end air removal from the second chamber. For still another example, walls of the first chamber can be transparent to allow visualization of the lung in the first chamber from outside the first chamber.

In another embodiment, a medical air leak modeling system includes a liquid-tight and air-tight chamber. The chamber is configured to have a liquid therein with a lung immersed in the liquid adjacent a bottom wall of the chamber, a top wall of the chamber includes a domed portion that allows for collection of air between the top wall and a top of the liquid in the first chamber, and a top of the domed portion has a port therein configured to allow the collected air to exit therethrough. The system also includes a pressure mechanism located outside of the chamber and configured to inflate and deflate the lung immersed in the liquid in the chamber. In response to the inflation and deflation, a leak present in the lung releases air from the lung into liquid and then into the domed portion.

The system can vary in any number of ways. For example, the system can include a balloon configured to be immersed in the liquid in the chamber, and the balloon can be configured to deflate from a default inflated state in response to the lung being inflated. For yet another example, the pressure mechanism can include at least one of a ventilator configured to provide oscillating positive pressure to the lung immersed in the liquid in the chamber, and a piston configured to provide negative pressure to the lung immersed in the liquid in the first chamber. For still another example, the system can include a second liquid-tight and air-tight chamber in fluid communication with the first chamber, a first pump configured to pump fluid through the port and into the second chamber, a sensor configured to sense a liquid fill level of liquid in the second chamber, and a control unit operatively coupled to the sensor and configured to, in response to the sensor sensing a threshold amount of change in the fill level, activate a second pump to cause the second pump to pump liquid from the first chamber to the second chamber.

In another aspect, a medical air leak modeling method is provided that in one embodiment includes circulating fluid between a first liquid-tight and air-tight chamber and a second liquid-tight and air-tight chamber. The first chamber has a lung therein that is immersed in liquid. The method also includes sensing with a sensor a liquid fill level in the second chamber, and, in response to the sensor sensing a threshold amount of change in the fill level, activating a peristaltic pump to cause the pump to pump liquid from the first chamber to the second chamber. The method also includes using an amount of rotation of the peristaltic pump in pumping the air from the first chamber to the second chamber to determine an amount of air that leaked from the lung during the circulation of fluid.

BRIEF DESCRIPTION OF DRAWINGS

This invention will be more fully understood from the following detailed description taken in conjunction with the accompanying drawings, in which.

DETAILED DESCRIPTION

Figure 1:
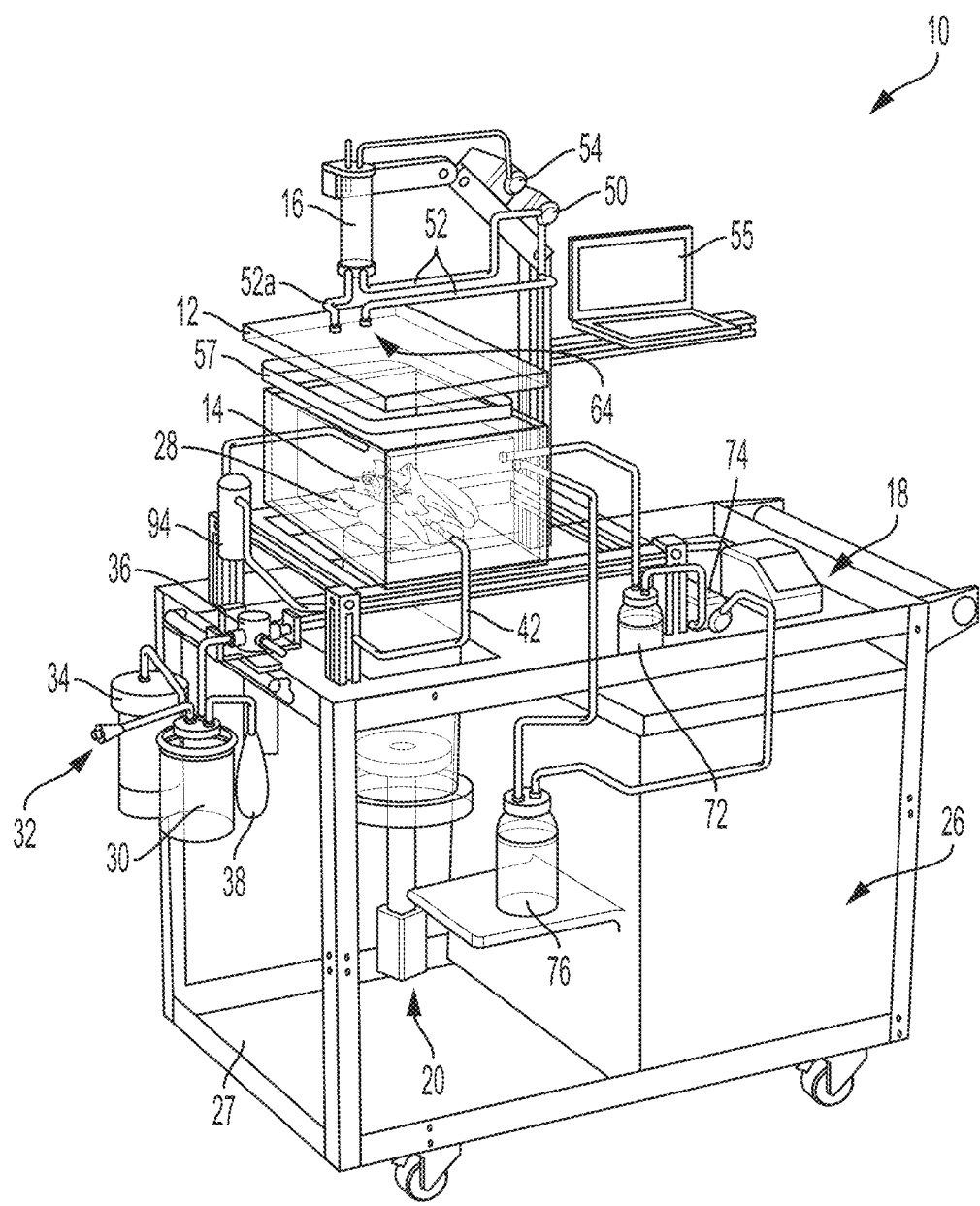
FIG. 1 is a schematic view of one embodiment of a model for modeling air leaks in lungs.

Certain exemplary embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. A person skilled in the art will appreciate that a dimension may not be a precise value but nevertheless be considered to be at about that value due to any number of factors such as manufacturing tolerances and sensitivity of measurement equipment. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

In general, systems, methods, and devices for modeling air leaks in lungs are provided. Embodiments of the systems, methods, and devices described herein may enable ex vivo perfusion and ventilation of lungs. The systems, methods, and devices described herein may serve as a viable test method for future prolonged air leak (PAL) studies. In an exemplary embodiment, to enable the clinically-relevant investigation of PAL etiology a model is configured to simulate in vivo lung mechanics and physiology of lungs, such as large animal lungs (e.g., porcine, etc.) and human lungs. The model may allow assessment of the impact of simulated surgical procedures across intra- and post-operative phases with the capability to maintain lung function. Various features of the model may facilitate this assessment, including the ability to directly visualize the lungs, to capture and quantify lung air leaks, to perform both mechanical (positive pressure) and physiological (negative pressure) ventilation, and to simulate coughing.

Figure 2A:
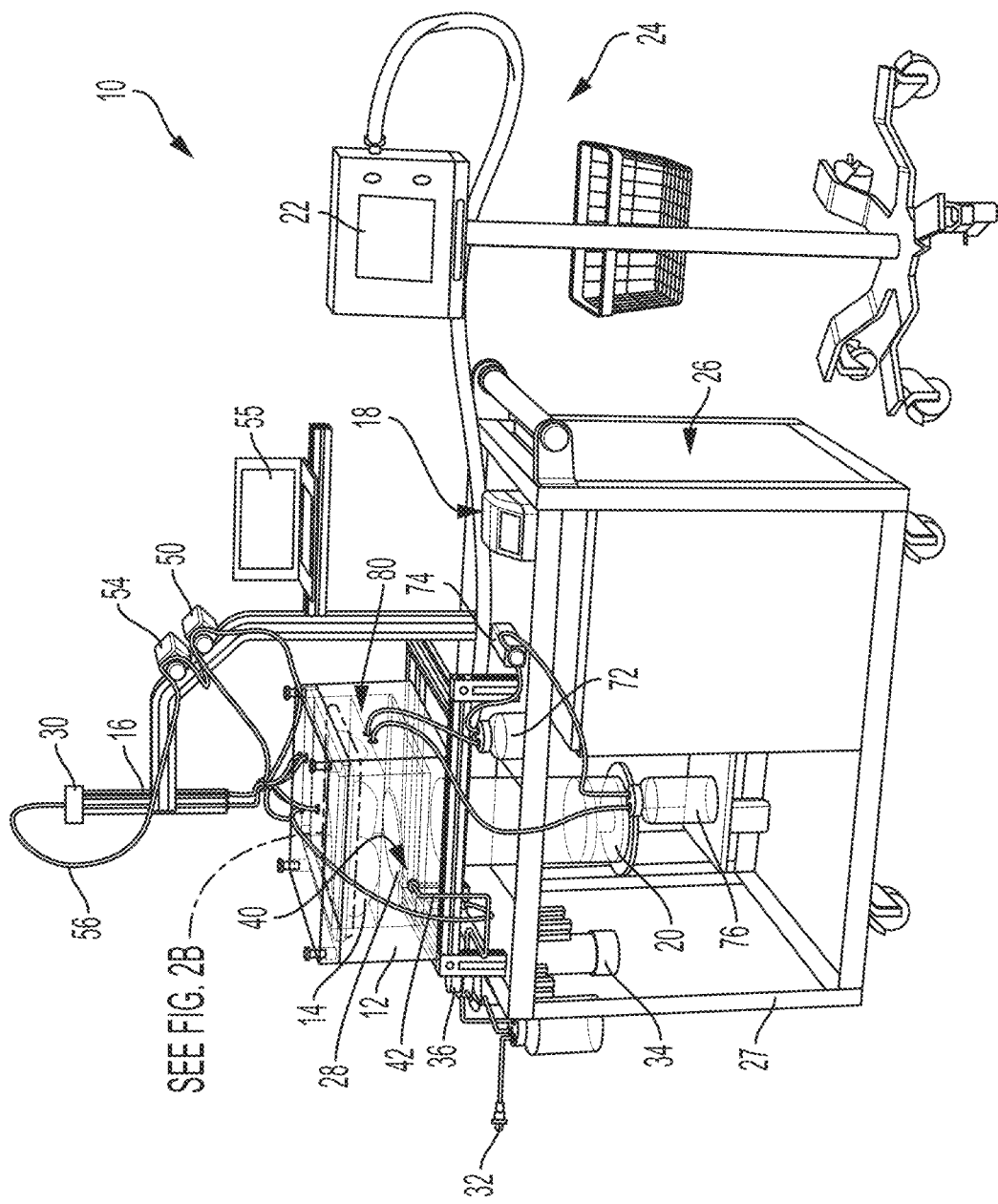
FIG. 2A is another schematic view of the model of FIG. 1.
Figure 2B:
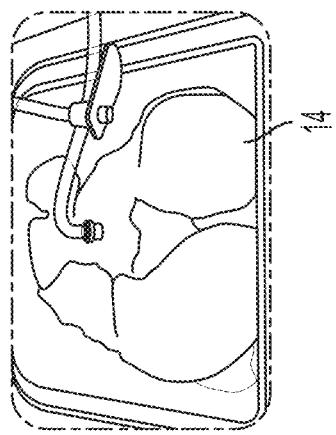
FIG. 2B is a schematic view of a portion of FIG. 2A.
Figure 3:
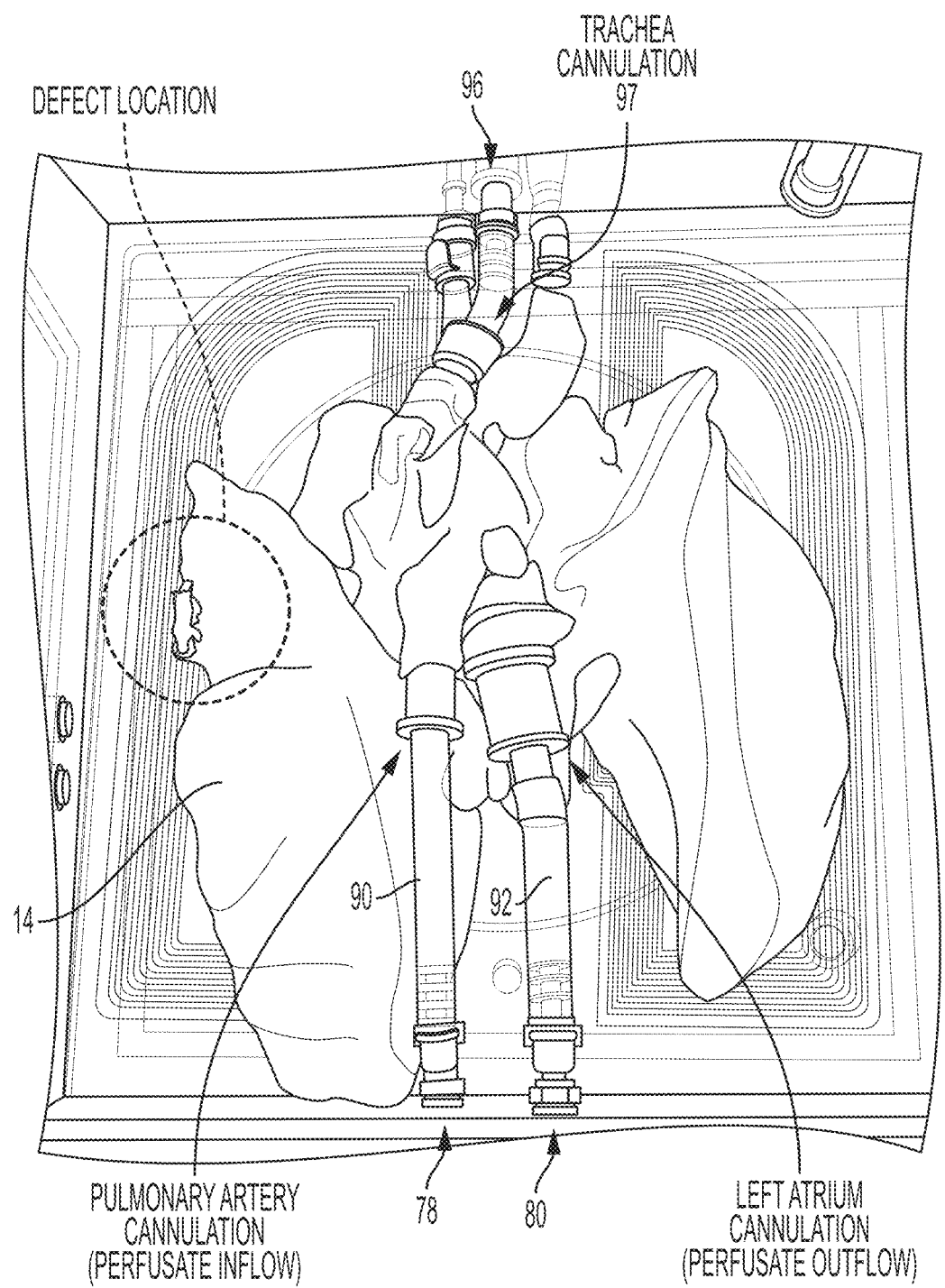
FIG. 3 is a top view of lungs in a first chamber of the model of FIG. 1.

FIGS. 1 and 2A illustrate one embodiment of a model 10 configured to allow for modeling of air leaks in lungs. The model 10 includes a first chamber 12 configured to have a lung 14 disposed therein ex vivo. A wall of the first chamber 12, the top wall in this illustrated embodiment, is configured to be removable and replaceable to allow the lung 14 to be disposed in and removed from the first chamber 12. The lung 14 in this illustrated embodiment is a pair of lungs, as shown in FIGS. 2A, 2B, and 3, which accurately reflects anatomy of typical patients. The model 10 also includes a second chamber 16 in fluid communication with the first chamber 12, a pressure mechanism configured to simulate breathing, and an electronics module 26 housing various electronic components therein that are configured to control various elements of the model 10 and to facilitate identification and analysis of an air leak in the lung 14. One or more pressure mechanisms can be used. In an exemplary embodiment, as discussed further below, the model 10 includes a first pressure mechanism 18 configured to provide positive pressure to the lung 14 to simulate mechanically assisted breathing, e.g., ventilator breathing, such as when a patient in undergoing a surgical procedure in an operating room, and the model 10 includes a second pressure mechanism 20 configured to provide negative pressure to the lung 14 to simulate physiological, natural, non-mechanically assisted breathing. In other embodiments, a model can include only one of the first pressure mechanism and the second pressure mechanism.

Each of the first and second chambers 12, 16 is configured to have liquid, e.g., saline or other liquid, therein. The lung 14 is immersed in the liquid in the first chamber 14 such that the lung 14 is completely submerged in the liquid. Each of the first and second chambers 12, 16 are liquid-tight and air-tight such that the first and second chambers 12, 16 define a closed fluid system. Providing a closed fluid system may facilitate detection of an air leak in the lung 14 by allowing for the isolation, collection, and quantification of air leaks in the lung 14 under the controlled pressure conditions in the first and second chambers 12, 16. Tubing extends between the first and second chambers 12, 16 to allow for circulation of fluid between the first and second chambers 12, 16, as discussed further below.

The first chamber 12 is transparent, e.g., has transparent walls, which facilitates visualization of the lung 14 disposed in the first chamber 12 and facilitates visualization of air bubbles in the liquid within the first chamber 12, e.g., visualization of air that escapes through a leak in the lung 14. Any of a variety of materials can be used for the transparent walls, such as polycarbonate or other material. The second chamber 16 is also transparent, which facilitates visualization of liquid within the second chamber 16. As discussed further below, a fill level of the liquid within the second chamber 16 can be sensed, e.g., using a level sensor 30, and used by electronics in the electronics module 20 in detecting presence of an air leak in the lung 14. Visualization of the liquid level in the second chamber 16 may allow for user observation and/or user verification of the liquid level in the second chamber 16.

Figure 4:
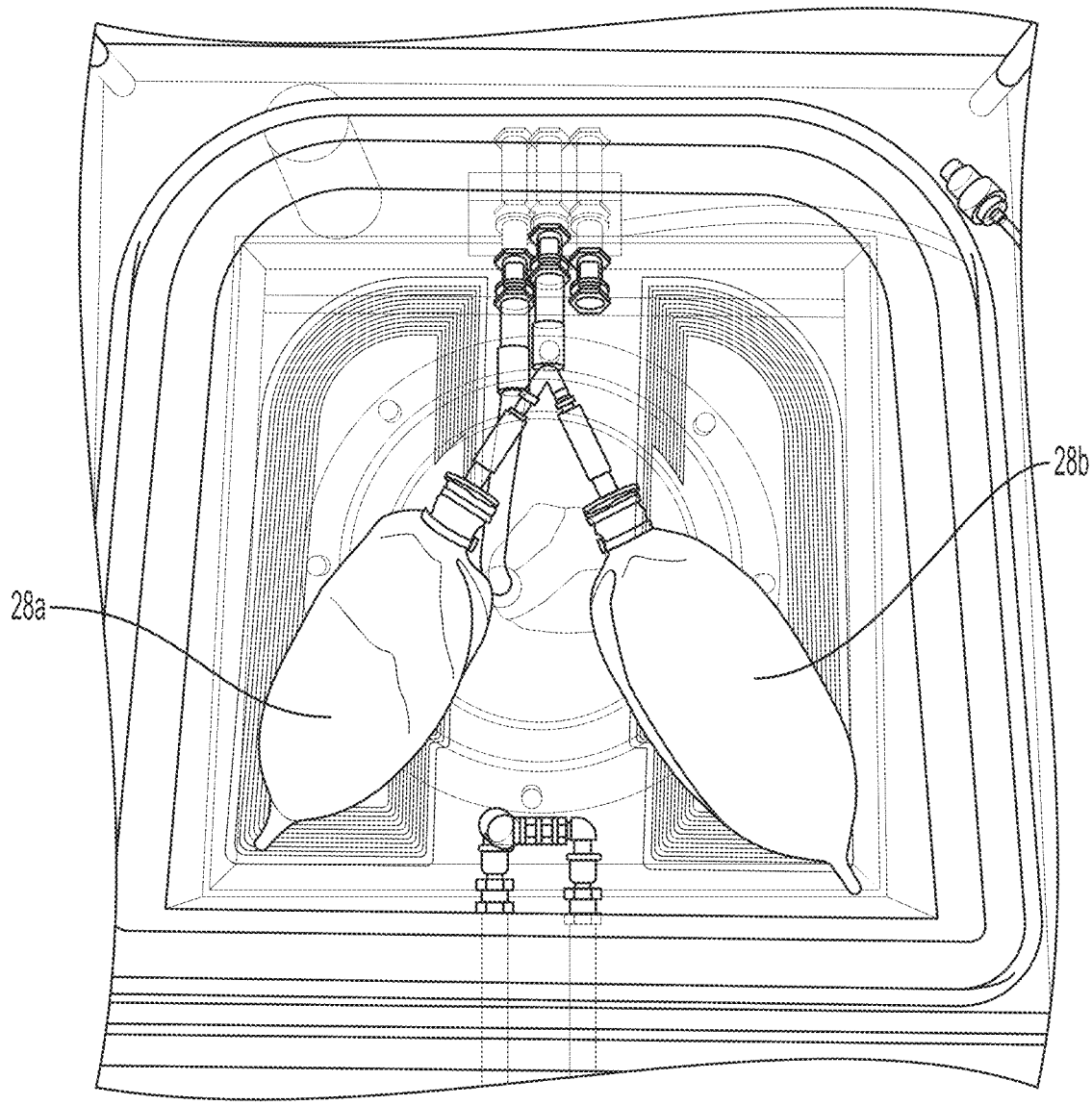
FIG. 4 is a top view of compression members in the first chamber of the model of FIG. 1.

The first chamber 12 is configured to have a compliance member 28 disposed therein that is immersed in the liquid in the first chamber 12. The compliance member 28 can have a variety of configurations, such as a balloon configured to compress (deflate) and decompress (inflate) or a bellows configured to compress (deflate) and decompress (inflate). In this illustrated embodiment, as most clearly shown in FIG. 4, the compliance member 28 is a balloon that includes first and second balloons 28a, 28b, although any number of compliance members 28 (one or more) can be used.

In general, the compliance member 28 is a compliant element configured to compress and decompress in response to pressure changes within the closed system defined by the first and second chambers 12, 14. In this way, the compliance member 28 can accommodate the change in pressure within the first chamber 12 when the lung 14 inflates and deflates within the first chamber 12 by the compliance member compressing when the lung 14 inflates and decompressing when the lung 14 deflates. The compliance member 28 thus has a volume that is equal to or greater than a volume of air that moves into and out of the lung 14 during the simulated breathing so that the compliance member 28 can fully compensate for maximum inflation and maximum deflation of the lung 14.

The compliance member 28 may also help simulate compliance of a chest wall that the lung 14 would experience in vivo.

The compliance member 28 is located below the lung 14 in the first chamber 12, e.g., closer to a bottom wall of the first chamber 12 than the lung 14 is to the first chamber's bottom wall. This location of the compliance member 28 relative to the lung 14 allows for hydrostatic pressure to be above the compliance member 28 within the first chamber 12. The first chamber 12 thus has a size large enough to contain the lung 14 and the compliance member 28 therein and to contain enough liquid in which to fully submerse the lung 14 and the compliance member 28. In this illustrated embodiment the first chamber 12 is approximately 15 L, although other sizes can be used. A person skilled in the art will appreciate that a specific parameter may not have a precise numerical value but nevertheless be considered to be "approximately" that specific numerical value due to one or more factors, such as manufacturing tolerances and sensitivity of measuring equipment. The first chamber 12 can have shelves therein to seat each of the lung 14 and the compliance member 28.

The compliance member 28 can be formed of any of a variety of materials. The material(s) forming the compliance member 28 should be compliant enough for the compliance member 28 to be able to compress and decompress in response to the lung's inflation and deflation.

Figure 5:
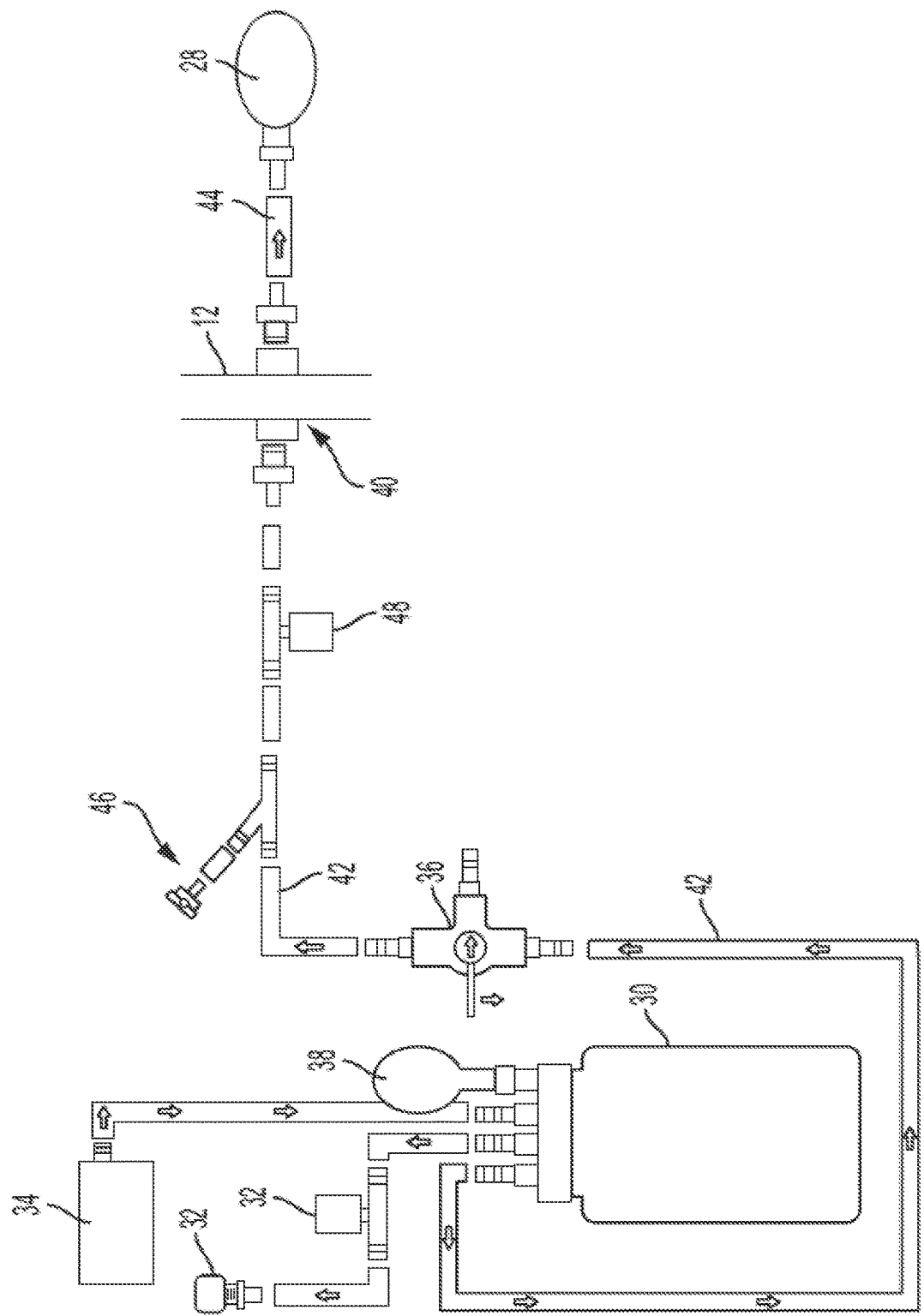
FIG. 5 is a schematic view of a portion of the model of FIG. 1.

The compliance member 28 has a relatively low pressure therein to facilitate easy compression and decompression of the compliance member 28 in response to the lung's inflation and deflation. The model 10 includes set pressure system configured to maintain a set pressure within the compliance member 28. The set pressure can be different based on a clinical scenario being modeled, with different set pressures being used for, e.g., post-resection pleural spaces, pneumothoraxes, and pathological chest compliance. As shown in FIGS. 1, 2A, and 5, the set pressure system includes an air control valve 32, an air compressor 34 configured to provide a substantially constant pressure to the compliance member 28, and a reservoir 30 configured to dampen the air compressor 34. In this illustrated embodiment, the air control valve 32 includes an air compressor and PEEP valve, although other valves can be used. Arrows in the tubes illustrated in FIG. 5 show air flow direction therein.

The first chamber 12 has a port 40 in a wall thereof to allow air to flow from the set pressure system outside of the first chamber 12 to the compliance member 28 inside the first chamber 12. The port 40 is in a front side wall of the first chamber 12, although the port 40 can be in another wall of the first chamber 12. A tube 42 is connected to the port 40 and extends between the port 40 and the reservoir 30 to facilitate air flow between the reservoir 30 and the port 40. Another tube 44 is located within the first chamber 12 and extends between the port 40 and the compliance member 28 in the first chamber 12. The tube 42 outside the first chamber 12 has a pump attachment 46 coupled thereto that allows a pump to be selectively coupled thereto. The pump attached to the pump attachment 46 is configured to pump air from the set pressure system to the compliance member 28.

A pressure sensor 48 outside the first chamber 12 and along the flow path from the set pressure system to the compliance member 28 is configured to sense a pressure in the flow path, e.g., within the tube 42 outside the first chamber 12, which corresponds to a pressure in the compliance member 28.

A three way valve 36 located outside the first chamber 12 is coupled between the set pressure system and the compliance member 28. The three way valve 36 allows the set pressure system to be isolated or cut off from the compliance member 28 so air cannot flow from the set pressure system to the compliance member 28. When air is not flowing from the set pressure system to the compliance member 28 through the tube 42, the compliance member 28 can maintain the pressure previously set therein by the set pressure system while the pressure mechanism is being used to inflate and deflate the lung 14 in the first chamber 12. As shown in FIG. 5, two of the three way valve's valve openings are coupled to the tubes 42 connecting the set pressure system to the compliance member 28. The third valve of the three way valve 36 is open to the atmosphere.

As in this illustrated embodiment, a manually manipulatable compliance member 38, e.g., balloon, bellows, etc., can be operatively coupled to the reservoir 30. The manually manipulatable compliance member 38 is configured to be manually compressed, e.g., squeezed, pressed, etc., by a user to manually urge air from the reservoir 30 to the compliance member 28 in the first chamber 12 to inflate the compliance member 28. Release of the manually manipulatable compliance member 38 will allow the compliance member 28 in the first chamber 12 to deflate. Allowing a user to manually compress and decompress the compliance member 28 in the first chamber 12 allows the user to simulate various procedures and situations that can occur with lungs in an operating room (OR) or other setting where the lungs are irregularly compressing and decompressing.

Figure 6:
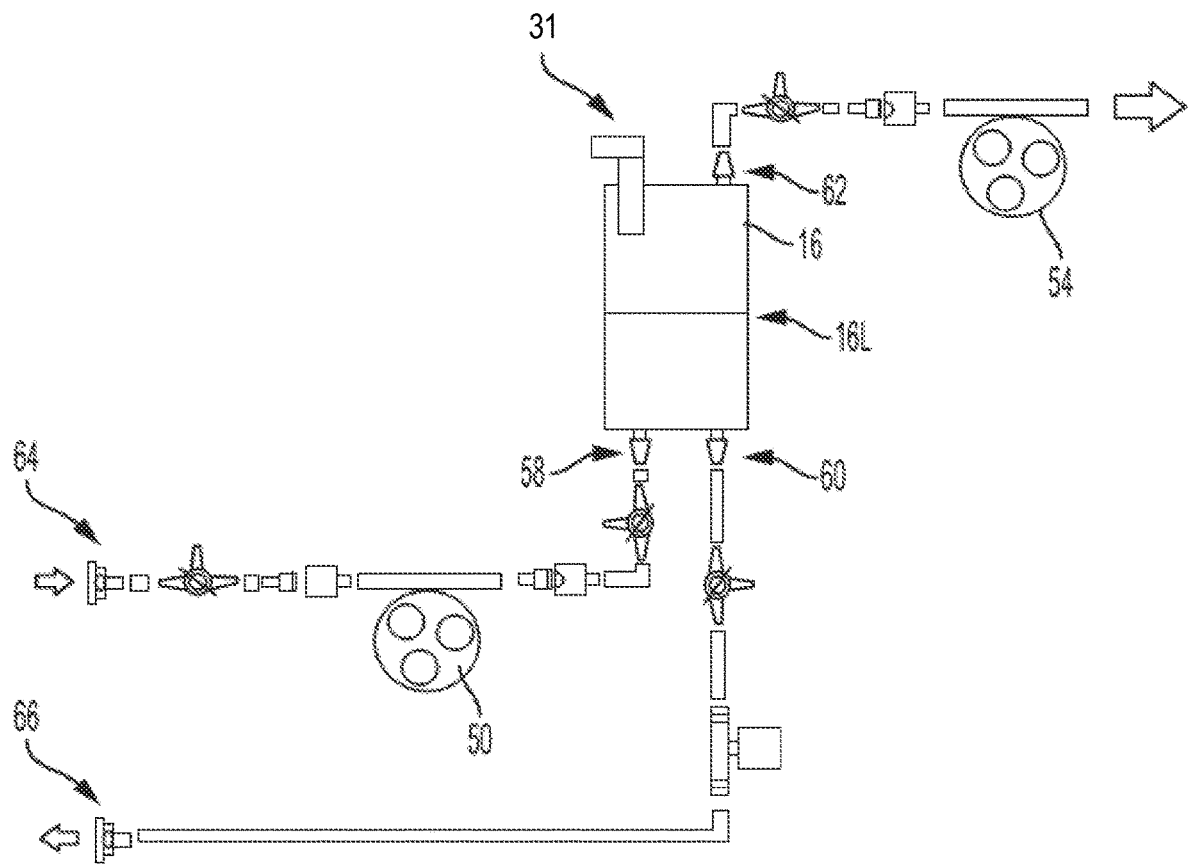
FIG. 6 is a schematic view of another portion of the model of FIG. 1.

First and second pumps 50, 54, shown in FIGS. 1, 2A, and 6, are configured to facilitate movement of liquid and air in the model 10. The first pump 50, also referred to herein as a fluid pump, is configured to circulate fluid between the first and second chambers 12, 16 via a tube 52 extending between the first chamber 12 and the fluid pump 50, a tube 52 extending between the first and second chambers 12, 16, and a tube 52 extending between the second chamber 16 and the fluid pump 50. When no air has leaked from the lung 14, the fluid pump 50 will only be circulating liquid between the first and second chambers 12, 14. As most clearly shown in FIG. 6, the fluid pump 50 is configured to pump fluid from the first chamber 12 via a port 64 in a top wall of the first chamber 12, into the second chamber 16 via a port 58 in a bottom wall of the second chamber 16, to pump fluid out of the second chamber 16 via a second port 60 in the bottom wall of the second chamber 16, and into the first chamber 12 via a second port 66 in the top wall of the first chamber 12. The first chamber's ports 64, 66 being in the top wall of the first chamber 12 helps ensure that any air that leaks from the lung 14 and rises as bubbles through the liquid in the first chamber 12 moves toward the ports 64, 66. The second chamber's ports 58, 60 being in the bottom wall of the second chamber 16 helps ensure that liquid is drawn out of the second port 60 and that any air that enters the second chamber 16 through the first port 60 rises up toward a top wall of the second chamber 16.

When air has leaked from the lung 14, the leaked air will be pumped along with liquid from the first chamber 12 to the second chamber 16. The second pump 54, also referred to herein as an air removal pump, is configured to remove air from the second chamber 16 by pumping liquid from the first chamber 12 into the second chamber 14. As most clearly shown in FIG. 6, the air removal pump 54 is configured to pump liquid into the second chamber 16 through a port 62 in the top wall of the second chamber 16, although other locations are possible.

In an exemplary embodiment, each of the pumps 50, 54 is a peristaltic pump. At least portions of the tubes at their respective pumps 50, 54 are flexible to facilitate flow therethrough, due to the pumps 50, 54 each being a peristaltic pump that rotates against their respective tubes to urge flow therethrough.

As mentioned above, the level sensor 30, e.g., an ultrasonic level sensor (such as UM121 Sick, Minneapolis, Minn.) or the like, operatively coupled to the second chamber 16 is configured to sense a fill level 16L of the liquid within the second chamber 16. The second chamber 16 is filled with liquid to a preset fill level. The preset fill level can vary. As one example, for a second chamber 16 having a volume of approximately 400 ml, the preset fill level can be a value selected in a range of 50 to 100 ml. The second chamber 16 can be filled to the preset fill level in a variety of ways, such as by air being pumped out of the second chamber 16 until the preset fill level is met.

Due to the first and second chambers 12, 16 defining a closed system, the fluid pump 50 circulating fluid between the first and second chambers 12, 16 will only change the fill level 16L of the liquid within the second chamber 16 when the circulated fluid includes air in addition to liquid. The level sensor 30 will thus not sense a change in the fill level 16L when only liquid is being circulated between the first and second chambers 12, 16. However, when the fluid pump 50 pumps air from the first chamber 12 into the second chamber 16 during the circulation of fluid, the air entering the second chamber 16 will displace liquid in the second chamber 16 and cause a change in the fill level 16L, namely cause the fill level 16L to drop or decrease within the second chamber 16. The level sensor 30 will thus sense a change in the fill level 16L when air enters the second chamber 16 from the first chamber 12. Air that enters the second chamber 16 from the first chamber 12 will rise as bubbles through the liquid in the second chamber 16 and toward the top port 62. Due to the first and second chambers 12, 16 defining a closed system, air entering the second chamber 16 from the first chamber 12 is indicative of an air leak in the lung 14, e.g., that the lung 14 has leaked air into the liquid in the first chamber 12. In response to the sensor 30 sensing the fill level change, the second pump 54 can be activated or turned on, e.g., in response to instructions from a controller in the electronic module 26 that is operatively connected to the sensor 30 and the second pump 54, to liquid from the first chamber 12 and into the second chamber 16 to restore liquid in the second chamber 16 to the preset fill level. The air removal pump 54 is configured to remain on until the level sensor 30 detects the fill level 16L at its original, preset fill level, thereby indicating that all air that entered the second chamber 16 from the first chamber 12 has been removed from the second chamber 16. The air removal pump 54 can then be deactivated or turned off, e.g., by the controller instructing the air removal pump 54 to turn off.

An amount of air removed from the first chamber 12 can be determined, e.g., by the controller, using an amount of rotation of the peristaltic air removal pump 54 during its operation to pump liquid into the second chamber 16. A size of the tube engaged by the air removal pump 54 is a known value. The air removal pump's rotations per minute (RPM) is also a known value, e.g., a known set value in a range of 6 to 600 RPM. Thus, by measuring the air removal pump's RPMs when the air removal pump 54 is on an amount of air that entered the second chamber 16 from the first chamber 12 during the fluid pump's circulation of fluid can be determined by simple calculation using the known size of the tube and the measured RPMs. Air leak average over time and total amount of air leaked over the lung's model use can also be simply calculated, e.g., by the controller. The controller can be configured to automatically receive RPMs from the air removal pump 54 during its rotation and can have the tube size preprogrammed in a memory in the electronics module 26 and operatively coupled to the controller.

The model 10 can be configured to measure lung ventilation during inflation/deflation of the lung 14. Lung ventilation can be measured in any of a variety of ways, such as by using electrical impedance, xenon-gas contrast enhanced CT, or hyperpolarized xenon or helium gas enhanced MRI scans. As shown in FIG. 1, to facilitate the measurement of lung ventilation, the model 10 includes an electrical impedance tomography (EIT) array 57 in a ring shape. The EIT array 57 includes thirty-two electrodes in this illustrated embodiment, but another number of electrodes can be used. As will be appreciated by a person skilled in the art, the EIT array 57 is configured to allow for real-time imaging of air distribution in the lung 14 during the lung's inflation and deflation. The EIT array 57 is operatively connected to the controller of the electronics module 26 to allow the controller to receive and analyze signals from the EIT array to provide for the real-time imaging. The real time images can be displayed on a display, such as on a display 55.

In an exemplary embodiment, the first chamber 12 is constructed to facilitate collection of air at a top thereof to help air leaked from the lung 14 be drawn out of the first chamber 12 by the fluid pump 50. The first chamber 12 being level, with respect to the ground, helps direct air bubbles to the top of the first chamber 12. In other embodiments, the first chamber 12 can be titled, e.g., off-level with respect to the ground, to help direct air bubbles to a particular target area within the first chamber 12.

Figure 7:
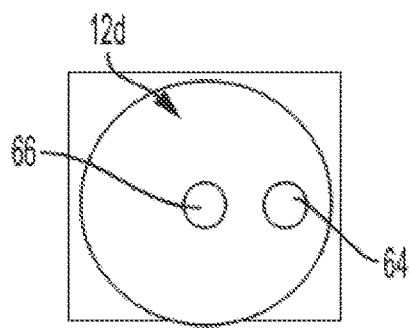
FIG. 7 is a schematic top view of a top wall of the first chamber of FIG. 1.

The top wall of the first chamber 12 has a dome shape on an internal surface thereof such that the internal top wall of the first chamber 12 has a curved concave shape, e.g., has a surface that is domed upwardly. An uppermost area within the volume of the first chamber 12 is thus defined by a peak of the dome shape in the first chamber's top wall. Any air that leaks from the lung 14 will rise as bubbles through the liquid in the first chamber 12 toward the uppermost area within the volume of first chamber 12, which will be the peak of the dome shape. The port 64 through which liquid and air is pumped out of the first chamber 12 is located on the dome shape, and in an exemplary embodiment, at the peak of the dome shape. Leaked air will thus naturally rise toward the port 64 and be more likely to be suctioned out of the first chamber 12 by the first pump 50 due to the air bubbles' proximity to the port 64. FIG. 7 illustrates the dome shape 12d of the first chamber's top wall with the ports 64, 66 located on the dome shape 12d.

Figure 8:
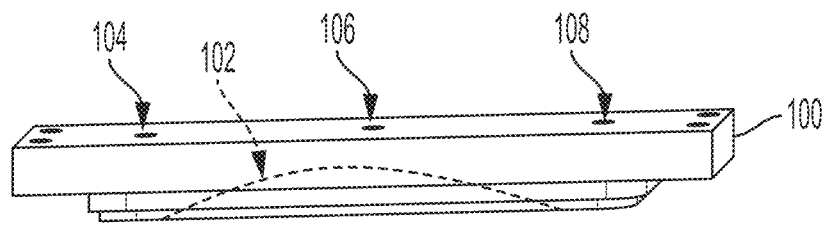
FIG. 8 is a perspective schematic view of another embodiment of a top wall of a first chamber of a model for modeling air leaks in lungs.
Figure 9:
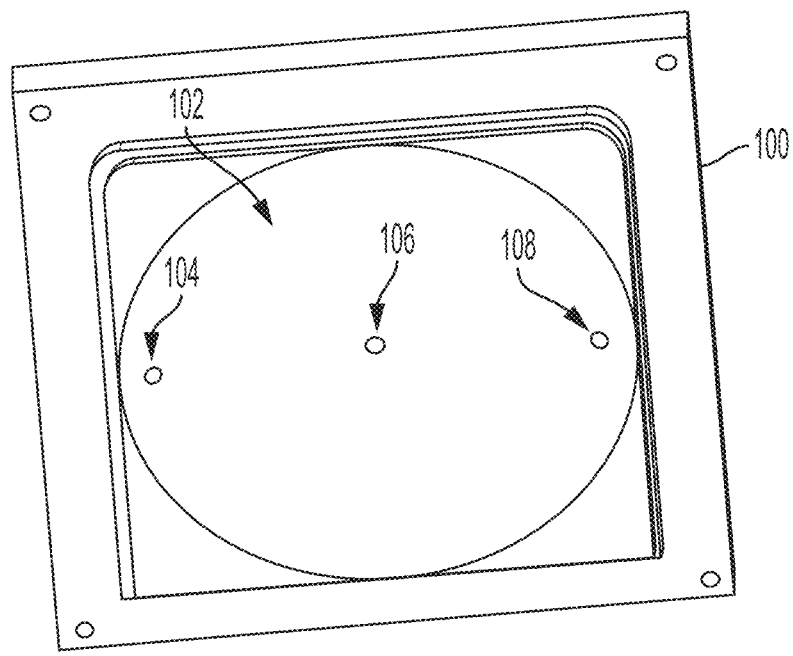
FIG. 9 is another perspective view of the top wall of FIG. 8.

FIGS. 8 and 9 illustrates another embodiment of a top wall 100 of a first chamber having a dome shape 102 therein at an internal surface thereof. The dome shape 102 is a curved concave shape that is domed upwardly similar to the dome shape in the top wall of the first chamber 12 of FIG. 1. The dome shape 102 of FIGS. 8 and 9 has three ports 104, 106, 108 located thereon. Only two of the ports 104, 106, 108 may be "active" with a tube connected thereto for fluid circulation between the first chamber and a second chamber fluidly coupled thereto similar to the first and second chambers 12, 16 of FIG. 1. The third, "inactive" one of the ports 104, 106, 108 will be closed or sealed to maintain the air-tight, liquid-tight nature of the first chamber. The tube through which liquid and air is pumped from the first chamber to the second chamber can be moved from one of the ports 104, 106, 108 to another one of the ports 104, 106, 108. This move can occur during use of the model, which can allow selection of a port 104, 106, 108 nearest an air leak in the lung based on a visualized location of an air leak in the lung through the transparency of the first chamber, e.g., based on seeing where air bubbles are rising from the lung. The leaked air may thus be more efficiently pumped out of the first chamber by being more closely located to the location where air bubbles are rising to the top of the first chamber.

It is possible that a lung disposed in the first chamber may have an unexpected, unintentional air leak therein that was caused during lung harvest or transport, as opposed to an air leak at an expected location on the lung such as along a staple line in the lung. Air leaks caused during lung harvest or transport are not typically of interest for study. Providing a top wall with multiple ports, such as the multiple ports 104, 106, 108 of FIGS. 8 and 9, the tube through which liquid and air is pumped from the first chamber to the second chamber can be positioned at the port closest to the expected location of the air leak (before or during use of the model) to help avoid collection and removal of air unrelated to the air leak of interest. A tube can be positioned at the port closest to the unexpected, unintentional air leak in the lung to collect and remove that leaked air from the first chamber to help avoid that air being considered in the identification and analysis of an expected air leak.

Figure 10:
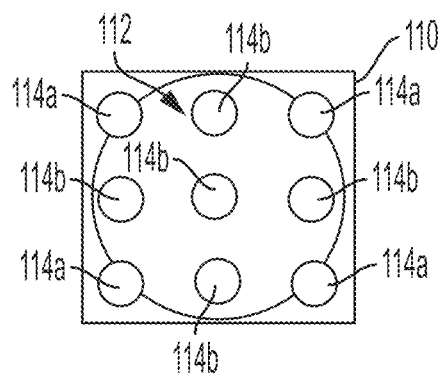
FIG. 10 is a schematic top view of another embodiment of a top wall of a first chamber of a model for modeling air leaks in lungs.

FIG. 10 illustrates another embodiment of a top wall 110 of a first chamber having a dome shape 112 therein at an internal surface thereof. The dome shape 112 is a curved concave shape that is domed upwardly similar to the dome shape in the top wall of the first chamber 12 of FIG. 1. The dome shape 112 of FIG. 10 has nine ports 114a, 114b located thereon. Four of the ports 114a are located partially on the dome shape 112, and five of the ports 114b are located entirely on the dome shape 112, similar to the ports 64, 66 of FIG. 7 and the ports 104, 106, 108 of FIG. 9 that are located entirely on their respective dome shapes. Similar to that discussed above regarding FIGS. 8 and 9, only two of the ports 114a, 114b may be "active" at any time, with the tube through which liquid and air is pumped from the first chamber to the second chamber being movable from one of the ports 114a, 114b to another one of the ports 114a, 114b, e.g., based on where air bubbles are seen to be rising toward the top wall 110.

Alternatively, more than two of the ports 114a, 114b can be "active" at the same time. Two of the ports 114a, 114b can be used for fluid circulation between the first chamber and the second chamber, while two others of the ports 104, 106, 108 can be used for fluid circulation between the first chamber and a third chamber using another fluid pump similar to the fluid pump used to circulate fluid between the first and second chambers. The third chamber is configured similar to the second chamber. The third chamber can thus, similar to the second chamber, be configured to receive air leaked from a lung in the first chamber and be used to identify and analyze air leaks similar to that discussed herein with respect to the second chamber. Allowing pumping out of the first chamber through more than one port 114a, 114b may facilitate efficient collection and removal of air leaked from a lung within the first chamber in the event of multiple air leaks in the lung and/or may prevent a user from having to manually move a tube between ports 114a, 114b during use of the model including the top wall 110. Providing that enough ports are available in the top wall, as in the illustrated embodiment of FIG. 10, one or more chambers in addition to the second and third chambers can be operatively connected to the first chamber similar to the second and third chambers.

The top walls of the first chambers of FIGS. 7, 9, and 10 each have a single dome shape therein. In other embodiments, a top wall of a first chamber can have multiple dome shapes therein. Each of the multiple dome shapes can have a curved concave shape that is domed upwardly similar to the dome shape in the top wall of the first chamber 12 of FIG. 1. Each of the multiple dome shapes can have at least one port located thereon. By providing multiple dome shapes in the top wall, air leaking from a lung within the first chamber will naturally rise toward a top of the dome shape nearest to the leak. Air leaked from the lung may thus be more efficiently collected and removed from the first chamber.

Figure 11:
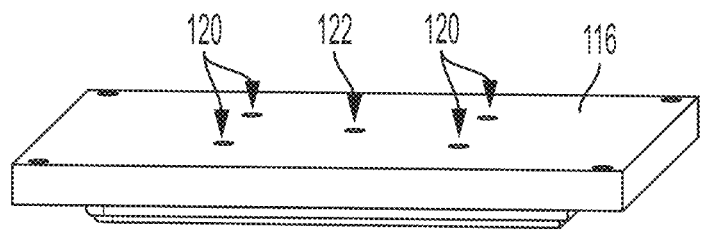
FIG. 11 is a perspective schematic view of yet another embodiment of a top wall of a first chamber of a model for modeling air leaks in lungs.
Figure 12:
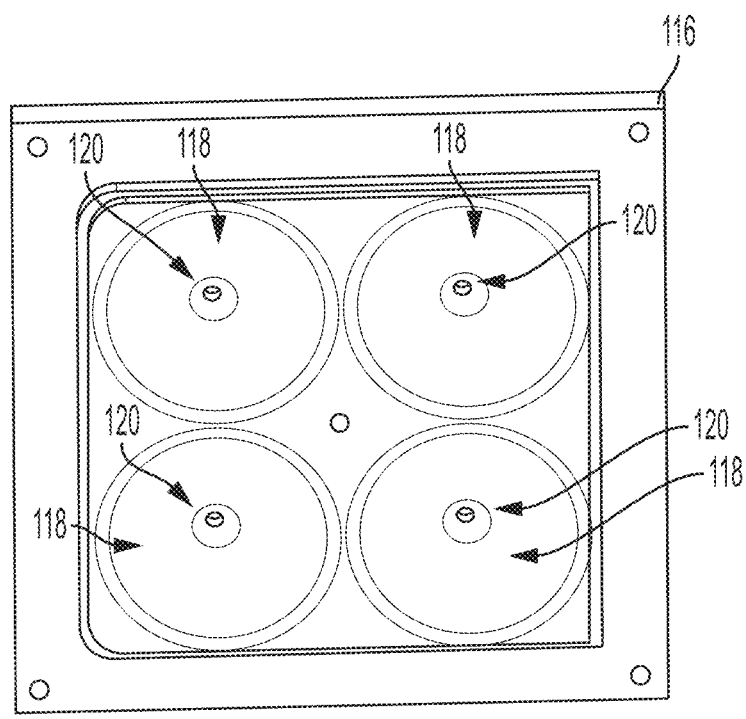
FIG. 12 is another perspective view of the top wall of FIG. 11.
Figure 13:
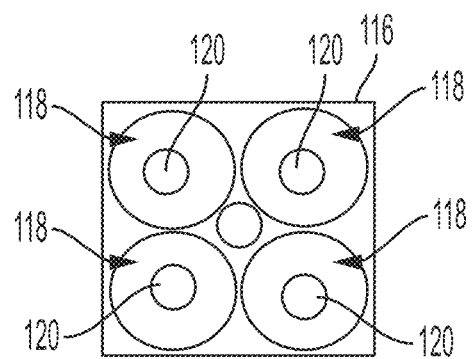
FIG. 13 is a schematic top view of the top wall of FIG. 11.

FIGS. 11-13 illustrate one embodiment of a top wall 116 having a plurality of dome shapes 118 in an internal surface thereof. The top wall 116 has four dome shapes 118 in this illustrated embodiment, but any plural number of dome shapes can be used. The dome shapes 18 are each a curved concave shape that is domed upwardly similar to the dome shape in the top wall of the first chamber 12 of FIG. 1. Each of the dome shapes 118 has a port 120 located thereon. The ports 120 are each at a peak of its respective dome shape 118 in this illustrated embodiment. The top wall 116 also has a port 122 formed therein that is not located on any of the dome shapes 118. The port 122 is centrally located on the top wall 116. Providing a centrally located port 122 may facilitate efficient collection of air leaked from a lung in the first chamber since air may tend to collect centrally at the top wall 116 of the first chamber. Similar to that discussed above, only two of the ports 120, 122 may be "active" at any time, or, alternatively, more than two of the ports 120, 122 may be "active" at any time.

The ports in a first chamber through which fluid flows can each be coupled to a protective member. The protective member is configured to allow fluid flow therethrough so fluid can enter or exit the port. The protective member is also configured to prevent tissue from passing therethrough to protect the port from having tissue enter the port and be moved to another chamber (or get stuck in a tube en route to the other chamber). The protective member may thus help prevent a lung disposed in the first chamber, or any tissue or other matter inadvertently released from the lung, from being suctioned through the port into another chamber.

Figure 14:
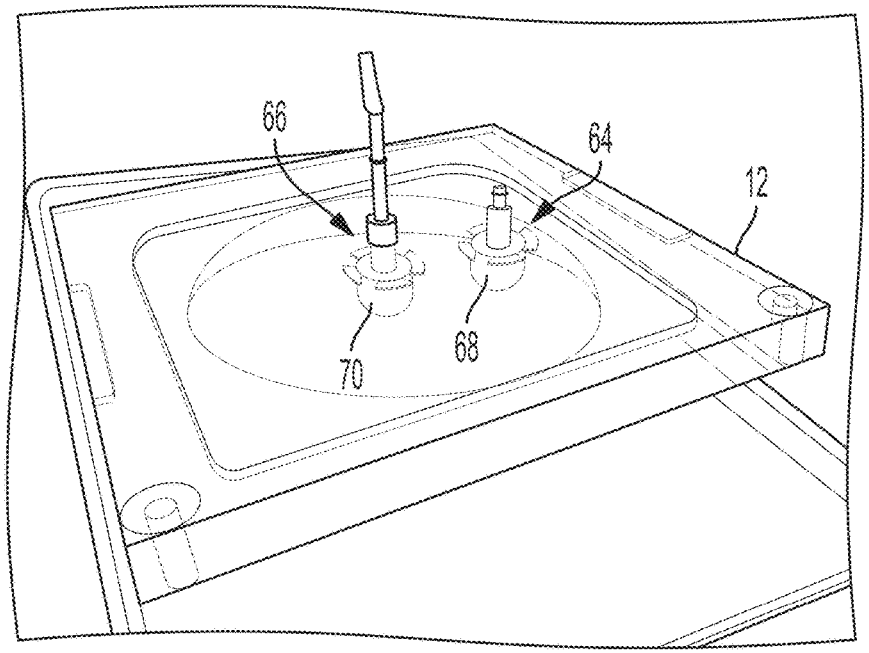
FIG. 14 is a perspective view of the top wall of FIG. 7.
Figure 15:
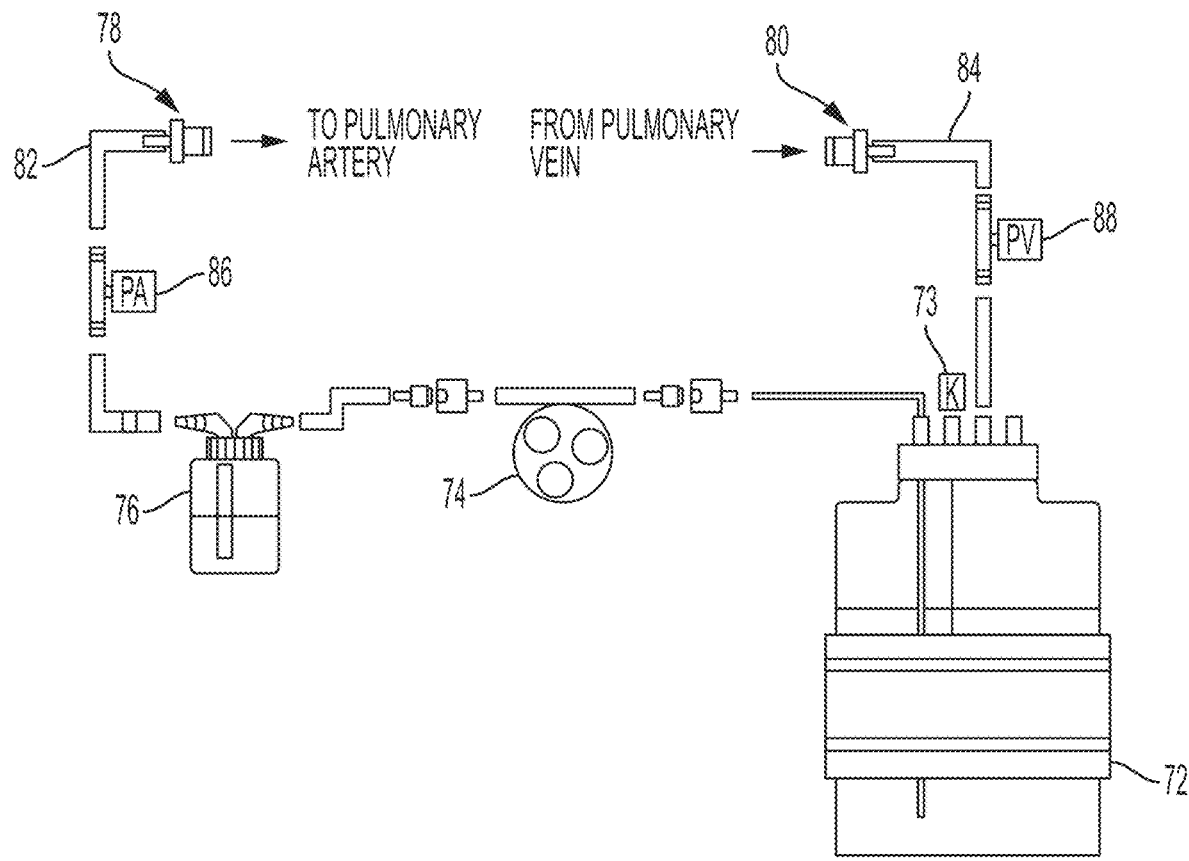
FIG. 15 is a schematic view of yet another portion of the model of FIG. 1.

FIG. 14 illustrates one embodiment of a protective member. Each of the ports 64, 66 of the first chamber 12 has a protective member 68, 70 coupled thereto. The protective members 68, 70 are each a cup having a plurality of small holes therein, similar to a sieve or strainer, that are configured to allow fluid flow therethrough while preventing larger matter from passing therethrough.

A model can include a perfusion system configured to simulate in vivo blood flow in a lung when the lung is ex vivo in the model's first chamber. In general, the perfusion system is configured to circulate a liquid through the lung using the natural anatomy of the lung. The perfusion system may help keep the ex vivo lung viable for modeling use for a longer period of time than if the perfusion system was not present in the model or is present but unused with a particular lung.

One embodiment of a perfusion system is illustrated with respect to the model 10 of FIG. 1 in FIGS. 1-3 and 15. The perfusion system includes a perfusate fluid reservoir 72, a perfusate fluid pump 74, and a dampening unit 76. In general, the perfusate fluid is configured to flow from the reservoir 72, through the dampening unit 76, through the lung 14, and back to the reservoir 72. The perfusate fluid can be any of a variety of fluids, such as saline or the like.

The reservoir 72 is configured to store fluid therein for circulation in the lung 14. The reservoir 72 is coupled to a heating element configured to heat the fluid therein. The heating element can have any of a variety of configurations, as will be appreciated by a person skilled in the art, such as a heating coil, a positive temperature coefficient (PTC) cable, a heating wrap, etc. A temperature sensor 73, e.g., a thermocouple or the like, is configured to sense a temperature of the perfusate fluid. The temperature of the fluid as sensed by the sensor 73 can be monitored, e.g., by the controller, for safety and/or for monitoring of modeling conditions.

The pump 74 is configured to pump fluid from the reservoir 72 toward the dampening unit 76. The pump 74 is a peristaltic pump in this illustrated embodiment, which may allow for quantification of an amount of perfusate fluid circulated through the lung 14 similar to that discussed above regarding quantification of air pumped out of the second chamber 16. The inflation and deflation of the lung 14 in the first chamber 12 will urge the perfusate fluid out of the lung 14 and back to the reservoir 72. The perfusate fluid pump 74 can also contribute to the urging of the perfusate fluid back to the reservoir 72.

The dampening unit 76 is configured to dampen the pulsing effect of the pump 74 on the perfusate fluid, which may help reduce trauma to the lung 14 and/or help the perfusate fluid more accurately mimic blood flow through the lung 14. The dampening unit 76 in this illustrated embodiment is a jar having an inlet through which the perfusate fluid enters the jar and an outlet through which the perfusate fluid exits the jar. The dampening unit 76 having a volume in which the perfusate fluid collects before exiting the dampening unit 76 helps dampen the perfusate fluid. A volume of air is thus present in the dampening unit 76 to facilitate the dampening.

The first chamber 12 includes a perfusate inflow port 78 and a perfusate outflow port 80 in a right side wall thereof, although the perfusate ports 78, 80 can be located in another wall of the first chamber 12. The perfusate inflow port 78 is coupled to the dampening unit 76 via a tube 82 located outside the first chamber 12. The perfusate outflow port 80 is coupled to the reservoir 72 via another tube 84 located outside the first chamber 12. A pressure sensor 86 is located along the inflow tube 82 to sense pressure of the perfusate fluid flowing into the lung 14, and another pressure sensor 88 is located along the outflow tube 84 to sense pressure of the perfusate fluid flowing out of the lung 14. Each of the pressure sensors 86, 88 can be capped with luer lock ports to allow for attachment of a syringe thereto. The syringe can be used to remove perfusate fluid during its flow, to allow for sampling thereof, and/or can be used to remove air from within the tubes 82, 84 without having to disconnect the tubes 82, 84 or open the first chamber 12.

An inflow cannula 90 located within the first chamber 12 is coupled to the inflow port 78, and an outflow cannula 92 located within the first chamber 12 is coupled to the outflow port 80. The inflow cannula 90 simulates the pulmonary artery and is coupled to the lung 14 to allow fluid flow into the lung 14 to simulate blood flow into the lung 14. The outflow cannula 92 simulates the left atrium and is coupled to the lung 14 to allow the fluid that entered the lung 14 through the inflow cannula 90 to exit the lung 14. The cannulas 90, 92 can be secured to the lung 14 with umbilical tape or other securing mechanism to help keep the cannulas 90, 92 in place during use of the model 10.

A model can include a chamber heating system configured to heat the chamber configured to have a lung disposed therein, e.g., the first chamber 12 of the model 10. The chamber heating system may help keep the ex vivo lung at body temperature to better simulate in vivo conditions and/or may help keep the ex vivo lung viable for modeling use for a longer period of time than if the chamber heating system was not present in the model or is present but unused with a particular lung. The chamber heating system can have a variety of configurations.

The embodiment of FIG. 1 includes a chamber heating system. The first chamber 12 has jacketed walls, e.g., two walls with a space therebetween, to allow a heating fluid to be circulated in the walls of the first chamber 12, thereby heating the first chamber 12 and the liquid and the lung 14 disposed therein. Only the four side walls of the first chamber 12 are jacketed, but any of the chamber's walls can be jacketed. The model 10 includes a heating fluid reservoir in communication with the space between the walls and a pump configured to circulate the heating fluid between the heating fluid reservoir and the first chamber 12. The controller can be configured to control the pump to control the heating fluid's circulation.

A model can be configured to simulate a cough to allow evaluation of effects of coughing on the lung 14, either before or after an air leak in the lung 14 is present. In the embodiment of the model 10 of FIG. 1, the model 10 is configured to simulate a cough using a pinch valve 94, e.g., a pinch valve solenoid (EPK-1502-NO; Takasago Electric, Nagoya, Japan) or the like. The cough simulation is configured to only be provided during negative pressure ventilation, e.g., during use of the second pressure mechanism 20, and not during positive pressure ventilation, e.g., during use of the first pressure mechanism 18.

The first chamber 12 includes a trachea port 96 in a back side wall thereof, although the trachea port 96 can be located in another wall of the first chamber 12. The trachea port 96 is coupled on one side thereof (within the first chamber 12) to a trachea cannula 97 configured to couple to the lung 14 and mimic a trachea that extends from the lung 14 in vivo. The trachea cannula 97 can be secured to the lung 14 with umbilical tape or other securing mechanism to help keep the trachea cannula 97 in place during use of the model 10. On an opposite side of the trachea port 96 (outside the first chamber), the trachea port 96 is coupled to a tube 98 leading to the pinch valve 94. The tube 98 extends through the pinch valve 94 and to a drip jar 99. The drip jar 99 is configured to collect excess liquid. A tube 98a extending from the drop jar 99 can extend to the atmosphere or to the ventilator.

A pressure sensor 95 is located along the tube 98 to sense pressure of the fluid flowing therethrough. The pressure sensed by the sensor 95 may help the controller in gauging intensity of the simulated cough.

Figure 17:
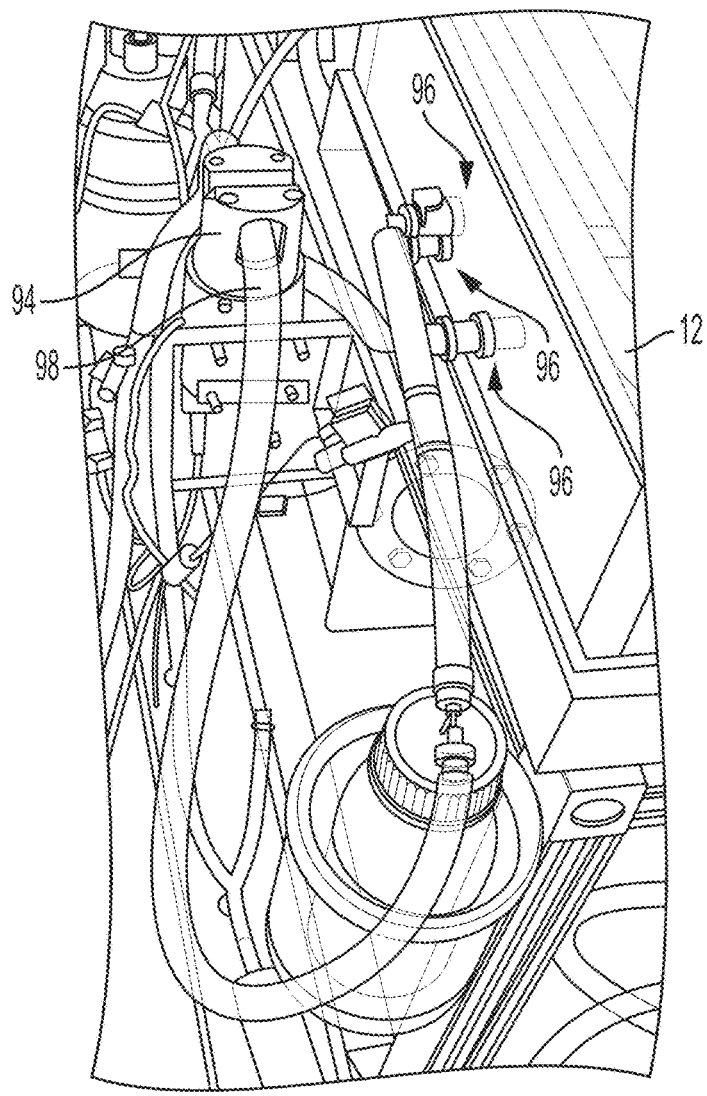
FIG. 17 is a schematic view of another portion of the model of FIG. 1.

In its default state the pinch valve 94 is open and does not pinch the tube 98. FIG. 17 shows the pinch valve 94 in its open state, not pinching the tube 98. Air can thus be "breathed" in by the lung 14 by air entering the lung 14 through the trachea port 96. To begin cough simulation, the pinch valve 94 is closed (either manually or via electronic control, such as by the controller), which pinches the tube 98 to obstruct fluid flow therethrough. Air therefore cannot enter the lung 14 through the trachea port 96 due to the pinched flow path. Pressure thus builds within the first chamber 12 outside of the lung 14 since air cannot be "inhaled" normally. When the pinch valve 94 is moved from being closed to being open, air will rush into the lung 14 through the trachea port 96 due to the built-up pressure in the first chamber 12. This rush of air into the lung 14 simulates a cough. The pinch valve 94 is configured to automatically open in response to the pressure sensor 95 sensing pressure equal to or above a predetermined cough pressure value. If the pressure is not sensed to be at or above the predetermined cough pressure value before the end of the instant "breathing" phase, the pinch valve 94 is configured to automatically open at the end of the phase to allow the next "breathing" phase to proceed normally. In other embodiments, the reverse can be done with opening of the pinch valve 94 causing a rush of air out of the lung 14 to simulate a cough.

As mentioned above, the pressure mechanism of the model 10 is configured to inflate and deflate the lung 14 in the first chamber 12 to facilitate air leak detection by simulating lung function during breathing, as air will escape out of the lung 14 during the simulated breathing if a leak is present in the lung 14. As also mentioned above, the model 10 in this illustrated embodiment includes two pressure mechanisms, a positive pressure mechanism (the first pressure mechanism 18) and a negative pressure mechanism (the second pressure mechanism 20), which allows for modeling of different breathing modalities. Being able to simulate different breathing modalities may allow the model 10 to identify different scenarios in which air leaks in the lung 14 are created or exacerbated and, accordingly, to allow for the development of solutions to prevent or correct such air leaks. Allowing for simulation of mechanically assisted breathing with the first pressure mechanism 18 may facilitate the identification of air leaks that occur during performance of a surgical procedure, including a location of air leaks in the lung 14 and/or a timing of when the air leaks in the lung 14 occur during the surgical procedure. For example, the model 10 can facilitate modeling of a lung during performance of a surgical procedure in which the lung is surgically stapled and a ventilator is used to assist in the patient's breathing during the surgical procedure. The model 10 may facilitate identification of where an air leak in the lung 14 occurs along the staple line and/or a timing of when the air leak occurs in the lung 14 after formation of the staple line. Allowing for simulation of non-mechanically assisted breathing with the second pressure mechanism 20 may facilitate the identification of air leaks in the lung 14 that occur following performance of a surgical procedure, including a location of air leaks in the lung 14 and/or a timing of when the air leaks in the lung 14 occur during the surgical procedure. For example, the model 10 can facilitate modeling of a lung after performance of a surgical procedure in which the lung is surgically stapled and the patient is breathing naturally without mechanical assistance after the surgical procedure has finished. In use, only one of the pressure mechanisms 18, 20 is on or active at a time.

Figure 16:
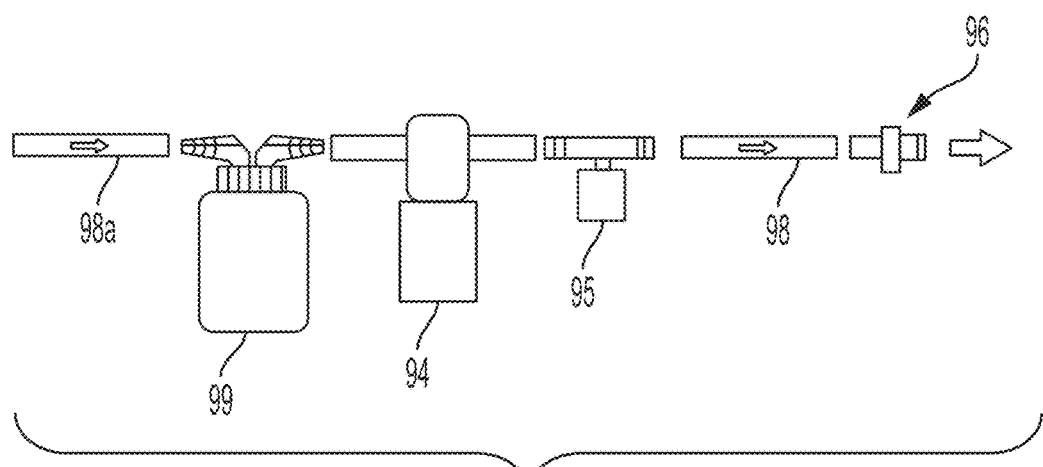
FIG. 16 is a schematic view of still another portion of the model of FIG. 1.

In general, the first pressure mechanism 18 is configured to push air into the lung 14 while enabling compensating volume change in the compliance member 28 as discussed above. The first pressure mechanism 18 is configured to operatively couple to the trachea port 96 to provide air to the lung 14. The first pressure mechanism 18 can be coupled to a tube 19 extending from the drip jar 99 (see FIG. 16) to facilitate this operative connection to the trachea port 96. The first pressure mechanism 18 includes a ventilator configured to provide oscillating positive pressure to the lung 14 immersed in the liquid in the first chamber 12. Any of a variety of ventilators can be used, such as Respironics Trilogy 200 (Respironics, Murraysville, Pa.) or other external clinical ventilator. FIG. 2A illustrates a display 22, mounted on a cart 24, that facilitates use of the first pressure mechanism 18, as will be appreciated by a person skilled in the art.

In general, the second pressure mechanism 20 is configured to induce a volume change in the liquid in the first chamber 12 which transmits to the lung 14, thereby pulling air into the lung 14. In this way, the second pressure mechanism 20 mimics a diaphragm's interaction with an in vivo lung. The second pressure mechanism 20 is configured to operatively couple to the trachea port 96 to provide air to the lung 14. The second pressure mechanism 20 can be coupled to the tube 19 extending from the drip jar 99 (see FIG. 16) to facilitate this operative connection to the trachea port 96. As shown in FIG. 3, three cannulas in the first chamber 12 extend from the trachea port 96 to the lung 14: one cannula operatively connected to the cough simulation tube 98 (see FIG. 16), one cannula operatively connected to the first pressure mechanism 18, and one cannula operatively connected to the second pressure mechanism 20. The trachea port 96 can thus include three separate ports, each configured to connect to one of the three cannulas, as shown in FIGS. 3 and 17.

Figure 18:
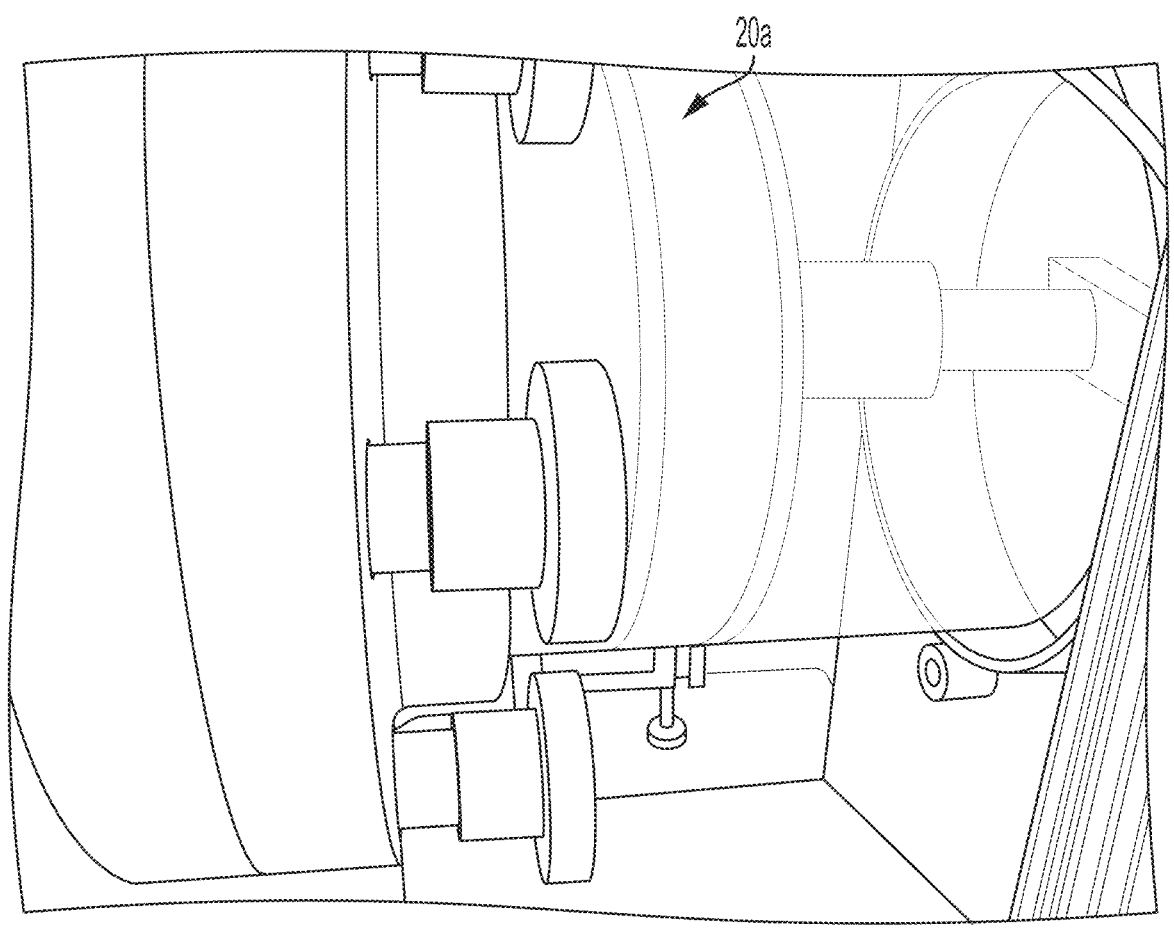
FIG. 18 is a perspective view of a piston of the model of FIG. 1.
Figure 19:
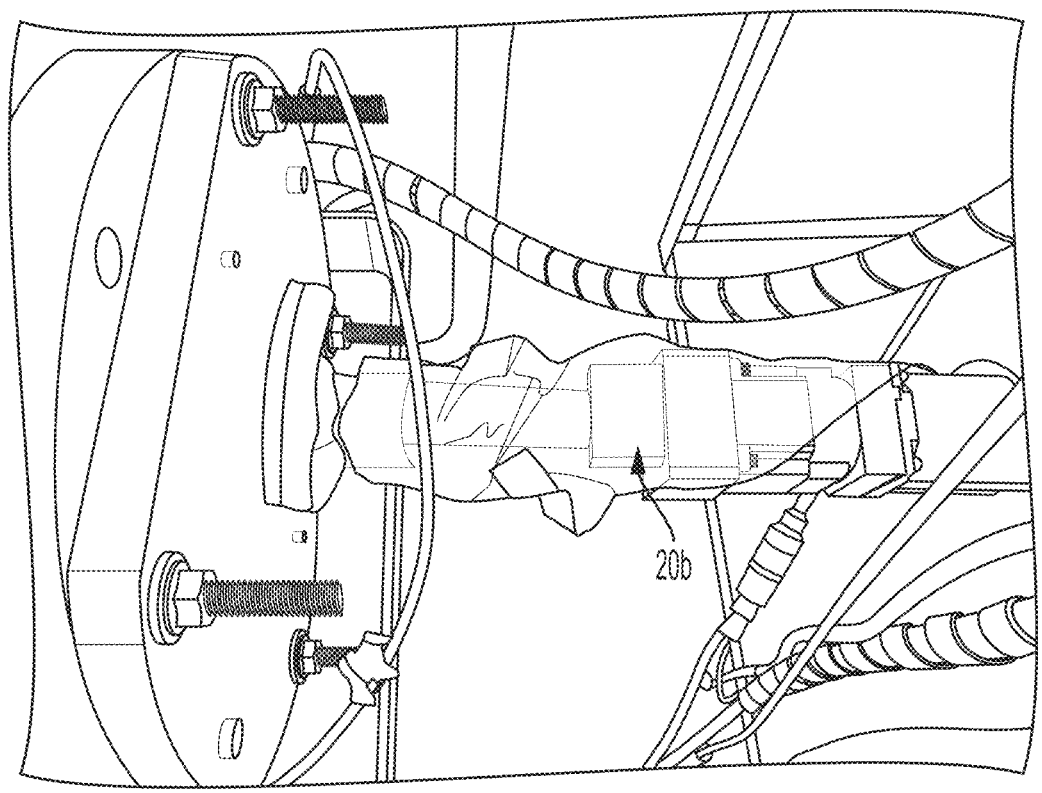
FIG. 19 is a perspective view of an actuator of the model of FIG. 1.

As shown in FIGS. 1 and 2A, the second pressure mechanism 20 includes a piston 20a (also see FIG. 18) and an actuator 20b (also see FIG. 19) configured to drive movement, e.g., oscillation, of the piston 20a. The movement of the piston 20a is configured to induce the volume change in the liquid in the first chamber 12. The actuator 20b can include any of a variety of motors or other drive mechanisms configured to cause movement of the piston 20a, such as a single axis actuator and servo drive controller (Tolomatic, Hamel, Minn.) or the like. The volume change induced by the second pressure mechanism 20 in the illustrated embodiment is a maximum of 2750 ml controlled in 1 ml steps across a range of approximately 4 to 570 ml/sec, but other volume changes are possible. The actuator 20b is configured to be operatively coupled to the controller in the electronics module 26 such that the controller can control actuation (e.g., turning on) and de-actuation (e.g., turning off) of the actuator 20b and thereby control the inflation/deflation of the lung 14.

The compliance member 28 does not compress/decompress when the second pressure mechanism 20 is being used because of the negative pressure induced, e.g., because air is being pulled out of the lung 14 instead of pushed into the lung 14 as with the first pressure mechanism 18. The compliance member 28 is deflated when the second pressure mechanism 20 is being used.

The model 10 can include an automatic shutoff mechanism as a safety feature for the second pressure mechanism 20. The automatic shutoff mechanism can be configured to turn off the actuator 20b to stop piston's movement in response to the piston 20a creating a pressure above a predetermined threshold of pressure, e.g., a pressure of 200 mmHg, a pressure value selected from a range of 15 to 930 psi, etc. The automatic shutoff mechanism can be implemented in a variety of ways, such as the controller being configured to turn off the actuator 20b in response to a pressure sensed by a pressure sensor. The automatic shutoff mechanism associated with the second pressure mechanism 20 can be provided in addition to a chamber pressure automatic shutoff mechanism that is similar to the automatic shutoff mechanism associated with the second pressure mechanism 20 but is configured to shut off whichever pressure mechanism 18, 20 is on in response to pressure in the first chamber 12 being sensed at a value equal to or greater than a predetermined threshold of pressure.

The piston 20a in the embodiment of FIGS. 1, 2, and 17 is in a vertical position relative to the first chamber 12, in which the lung 14 is in a horizontal position. In other embodiments a piston can be in a horizontal position relative to a first chamber with which the piston is operatively coupled. The piston being in a horizontal position relative to the first chamber may reduce an overall profile of the model, which may facilitate setup and/or portability of the model.

Figure 20:
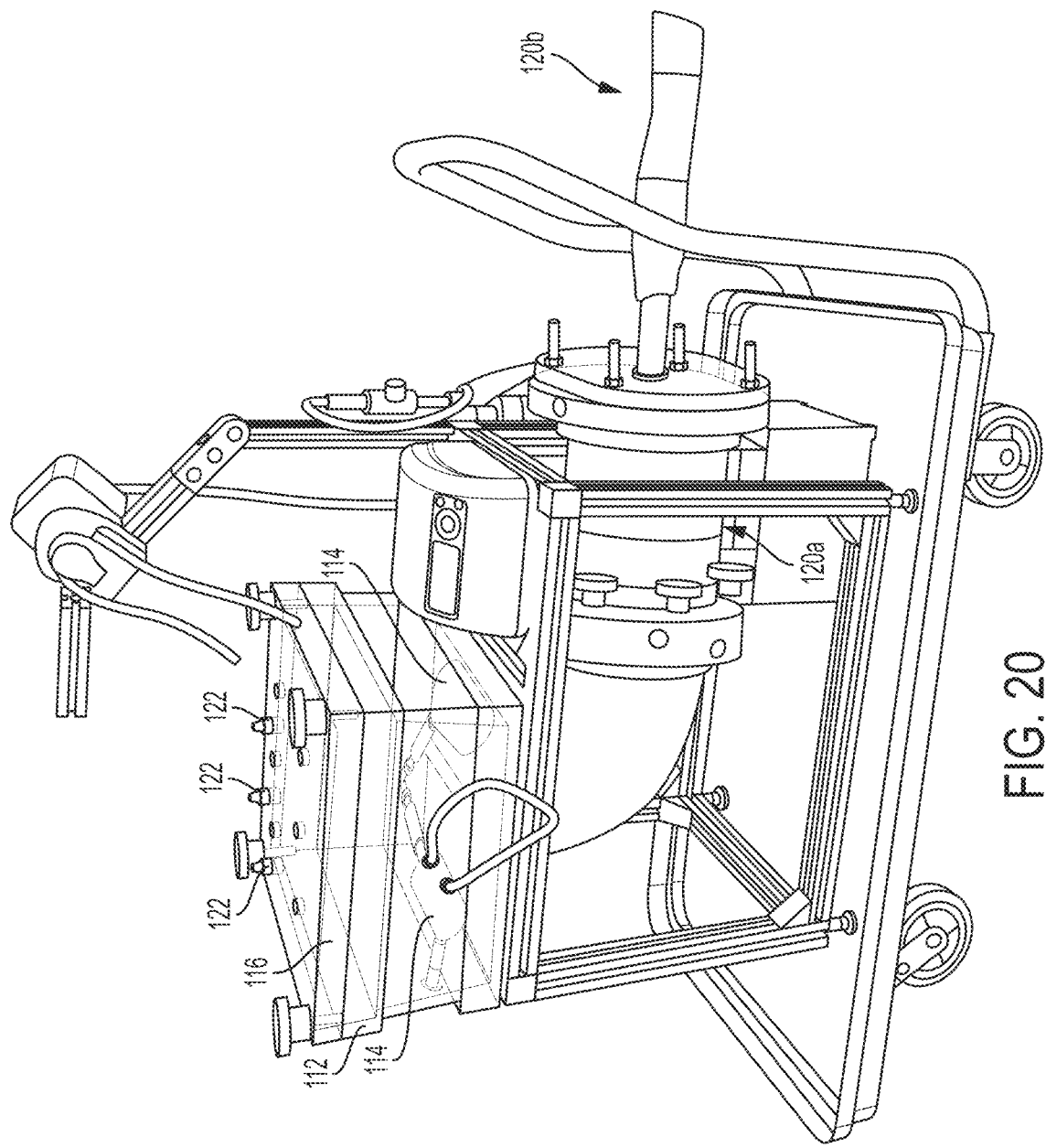
FIG. 20 is a perspective view of a portion of another embodiment of a model for modeling air leaks in lungs.

FIG. 20 illustrates one embodiment in which a piston 120a of a second pressure mechanism is in a horizontal position relative to a first chamber 112 with which the piston 120a is operatively coupled. FIG. 20 also shows an actuator 120b configured to drive movement of the piston 120a, three ports 122 in a top wall of the first chamber 112, two compliance members 114 within the first chamber 112, and a shelf 116 located above the compliance members 114 in the first chamber 112 and configured to seat a lung thereon.

FIG. 20 also illustrates another configuration of a chamber heating system. In this illustrated embodiment, each port through which liquid flows to enter the first chamber has a heating coil operatively coupled thereto. The heating coil is configured to heat the liquid flowing through its associated port. Each port through which liquid exits the first chamber, each port through which liquid enters the second chamber, and/or each port through which liquid exits the second chamber may also have a heating coil operatively coupled thereto to help facilitate heating of the liquid through its circulation path. The controller can be configured to control activation and deactivation of the heating coils.

FIG. 20 also illustrates an embodiment in which an electronics module is not located on a same cart as the liquid circulation portion of the model, e.g., the first and second chambers and associated tubing. Instead, the electronics module is located on its own cart or in another convenient location. The electronics module not being located on a same cart as the liquid circulation portion of the model may help protect the module's electronics from inadvertently coming into contact with liquid, may facilitate maintenance of the electronics including upgrades, may allow the first chamber to be at a lower, more user-accessible level since the electronics module need not be on the cart below the first chamber, and/or may reduce an amount of sanitization needed since the electronics module located away from the liquid circulation module need not be sanitized, unlike when the electronics module is on a same cart as the liquid circulation portion of the model.

As shown in FIGS. 1 and 2, the electronics module 26 in this illustrated embodiment of a model 10 is located on the same cart 27 as the liquid circulation portion of the model 10, e.g., the first and second chambers 12, 16 and associated tubing. The electronics module 26 being on the same cart 27 as the liquid circulation portion of the model 10 may ease setup of the model 10 and/or facilitate use of the model 10 in a variety of settings since the model 10 may be moved around as needed in a testing space.

The electronics module 26 can include a variety of electronics, such as a computer system includes a controller and a memory. One or more aspects or features of the computer systems described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

Figure 21:
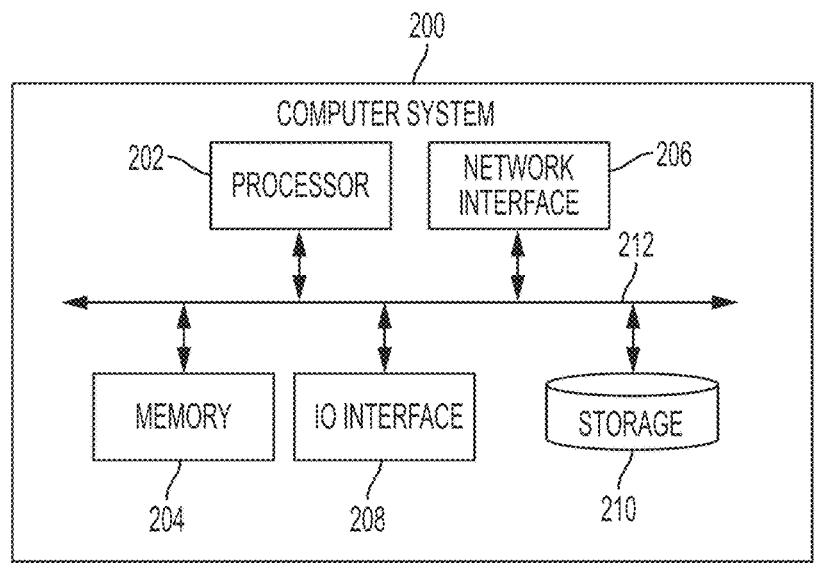
FIG. 21 is a schematic view of one embodiment of a computer system.

FIG. 21 illustrates one exemplary embodiment of a computer system 200. As shown, the computer system 200 includes one or more processors 202 which can control the operation of the computer system 200. "Processors" are also referred to herein as "controllers." The processor(s) 202 can include any type of microprocessor or central processing unit (CPU), including programmable general-purpose or special-purpose microprocessors and/or any one of a variety of proprietary or commercially available single or multi-processor systems. The computer system 200 can also include one or more memories 204, which can provide temporary storage for code to be executed by the processor(s) 202 or for data acquired from one or more users, storage devices, and/or databases. The memory 204 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 200 can be coupled to a bus system 212. The illustrated bus system 212 is an abstraction that represents any one or more separate physical busses, communication lines/interfaces, and/or multi-drop or point-to-point connections, connected by appropriate bridges, adapters, and/or controllers. The computer system 200 can also include one or more network interface(s) 206 that enable the computer system 200 to communicate with remote devices, e.g., motor(s) coupled to the drive system that is located within the surgical device or a robotic surgical system, one or more input/output (IO) interface(s) 208 that can include one or more interface components to connect the computer system 200 with other electronic equipment, such as sensors located on the motor(s), and one or more storage device(s) 210. The storage device(s) 210 can include any conventional medium for where VC is volume control mode, SIMV is synchronized intermittent-mandatory ventilation, and CPAP is constant positive airway pressure. Lungs were run under volume control either using the ventilator (positive pressure) or piston (negative pressure). Pressure-controlled SIMV was employed during the transition from full positive to full negative ventilation (Table 1). Leak rate was measured throughout the duration of the simulated procedure. Trachea flow rate, trachea volume, air leak rate, tissue temperature, perfusate temperature, transpulmonary pressure, chamber pressure, tracheal pressure, arterial and venous perfusion pressure, and vascular resistance (during perfusion) were collected at 20 Hz during testing.

TABLE 1

| | Peri-Operative Phase | Duration | Chest Compliance (Y/N)? | Ventilator Settings | Piston Settings |
|---|---|---|---|---|---|
| Full Positive Pressure | Open Chest | 10 Minutes | YES | VC = 800 ml, PEEP = 3 cm H20, Rate = 10 br/min | Off |
| | Closing Chest | <5 Minutes | YES | VC = 800 ml, PEEP = 3 cm H20, Rate = 10 br/min | Off |
| | Closed Chest | 10 Minutes | YES | VC = 800 ml, PEEP = 3 cm H20, Rate = 10 br/min | Off |
| Mix of Positive and | Reversal of Paralytics | 10 Minutes | YES | VC = 800 ml, PEEP = 3 cm H20, Rate = 10 br/min | VC = 150 ml, Rate = 5 br/min |
| | Emergence | 10 Minutes | YES | SMIV PIP = 25 cm H20, PEEP = 5 cm H20, Rate = 10 br/min | VC = 400 ml, Rate = 10 br/min |
| | Spontaneous Ventilation | 10 Minutes | YES | SMIV PIP = 25 cm H20, PEEP = 5 cm H20, Rate = 10 br/min | VC = 800 ml, Rate = 10 br/min |
| Full Negative Pressure | Post-Extubation | 15 Minutes | NO | CPAP = 5 cm H20 | VC = 800 ml, Rate = 10 br/min |
| | Coughing | 5 Minutes | NO | CPAP = 5 cm H20, 5 cough/min | VC = 800 ml, Rate = 10 br/min |
| | Deep Breath | 5 Minutes | NO | CPAP = 5 cm H20 | VC = 1200 ml, Rate = 10 br/min | storing data in a non-volatile and/or non-transient manner. The storage device(s) 210 can thus hold data and/or instructions in a persistent state, i.e., the value(s) are retained despite interruption of power to the computer system 200.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

EXAMPLES

The accuracy of the air leak quantification system of FIG. 1 was assessed with a leak removal test of n=18 trials, conducted using a 600 ml calibration syringe (Biopac; San Diego, Calif.) to inject a bolus of air which was subsequently cycled into the leak chamber, removed, and quantified over an average duration of 36 seconds. Since air delivery rates were variable for each trial, each dataset was normalized by time and leak volumes at regular normalized intervals (0, 0.1, 0.2, etc.) were averaged.

A protocol was designed to serve as a baseline testing routine to mimic clinical procedures. Porcine lungs were taken though a simulated perioperative procedure over the course of 80 minutes, with phases shown below in Table 1, Nine porcine lungs (Midwest Research Swine; Gibbon, Minn.) were harvested, flushed with heparinized saline, and shipped overnight on wet ice for testing in the system. The pulmonary artery (PA) and left atrium (LA) cannulas were attached and deaired using an in-house formulated perfusate similar to commercially available Perfadex. The trachea cannula was attached proximal to the cranial lobe airway bifurcation. Lungs were slowly warmed in a water bath and were gently inflated using an Ambu bag attached to the tracheal cannula until the lungs were recruited. Upon recruitment, a 0.5 mm deep defect was created in the right cranial lobes of each lung using a 20-gauge needle, resulting in an approximate leak of 100-250 ml/min. Lungs were placed in a partially-filled chamber with saline maintained at 37° C. With the chamber lid open, testing progressed for ten minutes in an open chest/mechanical ventilation phase. An approximately five-minute chamber closing phase (simulating surgical closure of the chest) was conducted, followed by a ten-minute closed chest/mechanical ventilation phase. Emergence from paralysis/anesthesia (shallow negative pressure ventilation with full mechanical support) and spontaneous ventilation (full negative pressure ventilation with full mechanical support) were simulated for ten minutes each, while post-extubation (full negative pressure ventilation with no mechanical support) was simulated for fifteen minutes. A five-minute intermittent coughing phase (five coughs/min) was then simulated, followed by a five minute deep breathing phase (150% baseline volume). Because leak rates could show variability between specimens, a normalized value was computed based on the maximum ($x_{max}$) and minimum ($x_{min}$) leak rate values for a given specimen, as described by the following equation, where $x_{max}$ and $x_{min}$ were found for each specimen across the entire testing protocol (these maximum and minimum values represent the maximum and minimum across all testing phases for each tested lung):

$$x_{norm} = \frac{(x - x_{min})}{(x_{max} - x_{min})}$$

Using electrical impedance tomography (EIT), ventilation was monitored during testing to ensure adequate air ventilation, especially in the right cranial lobe (site of defect). Impedance data was recorded at ten frames/sec and imported into the EIDORS software. Approximately ten respiratory cycles were cropped from the entire data file to facilitate single-cycle analysis. Using a masking tool within Matlab, right and left lung boundaries were hand selected from a peak impedance map from a given cycle. Single cycle impedance waveforms, right and left like quadrant impedance waveforms, and peak impedance (represented as % of tidal volume) were outputted. Perfusion was maintained at 250 ml/min with a 1 Hz sinusoidal waveform to simulate cardiac output. Perfusate baseline sample and LA outflow samples at five, ten, and fifteen minute intervals were collected from six lungs to monitor electrolytes and blood gasses such as $pCO_2$, $pO_2$, and pH, as well as glucose. An i-STAT handheld blood analyzer (Abbott, Ill. USA) and CG8+ cartridges (general blood gas panel analysis including glucose, pH, $pCO_2$, $pO_2$, and $HCO_3$) were utilized to perform the analysis.

Figure 22:
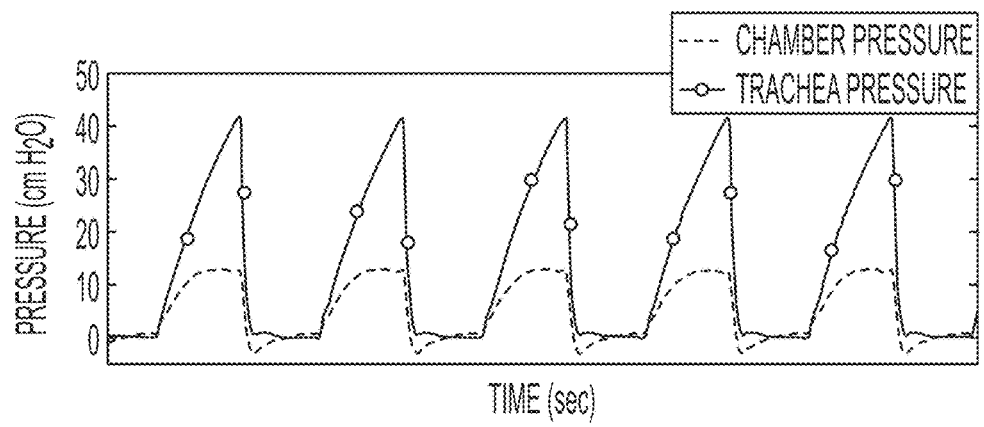
FIG. 22 is a graph showing closed chest chamber and trachea pressures vs. time.
Figure 23:
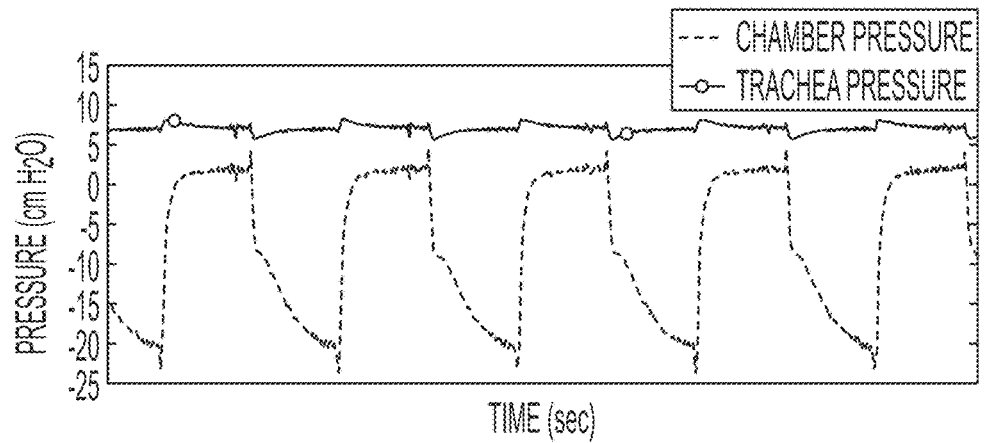
FIG. 23 is a graph showing post-extubation chamber and trachea pressures vs. time.

Ventilation flow, volume, and pressure were continuously recorded through all phases in the tested lungs. Representative pressure data points from the trachea, chamber (pleural space), PA, LA, and chest compliance balloons were plotted over the course of multiple breath cycles for closed chest (positive pressure ventilation) and post-extubation (negative pressure ventilation) phases, as shown in FIGS. 22 and 23. FIG. 22 shows a representative plot of tracheal and chamber pressures versus time collected during the closed chest phase (positive pressure ventilation). FIG. 23 shows a representative plot of tracheal and chamber pressures versus time collected during the post-extubation phase (negative pressure ventilation). Cycles from positive pressure (closed chest, full mechanical ventilation) and negative pressure (post extubation) phases were averaged for each tested lung.

Figure 24:
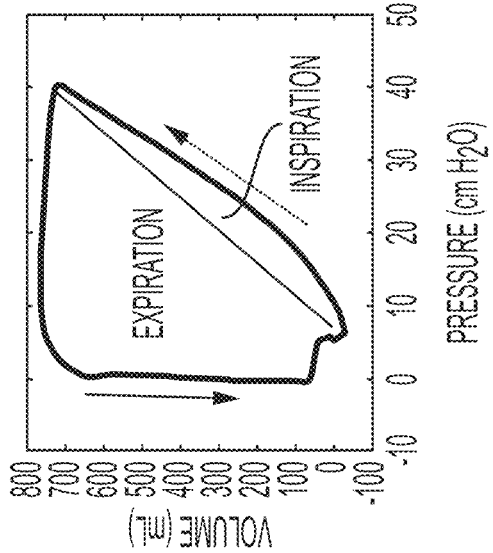
FIG. 24 is a plot showing mean flow-volume loop for closed chest (trachea)
Figure 25:
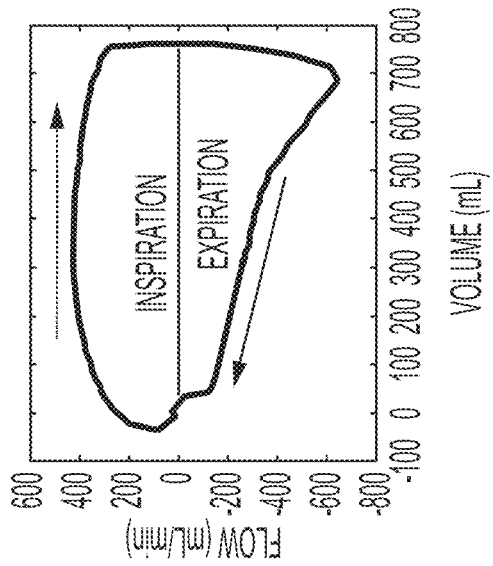
FIG. 25 is a plot showing mean volume-pressure loop for closed chest (trachea)
Figure 28:
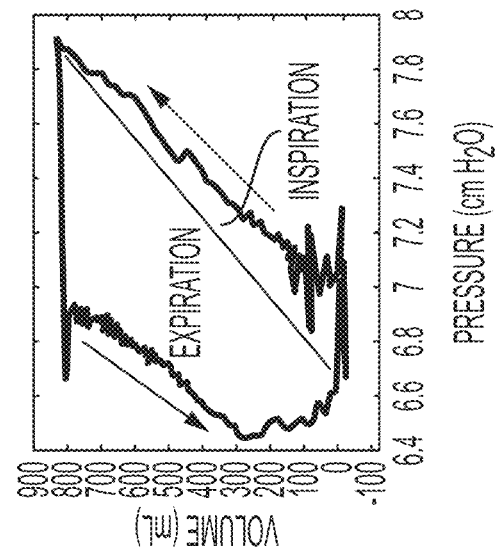
FIG. 28 is a plot showing mean volume-pressure loop for post-extubation (trachea)
Figure 27:
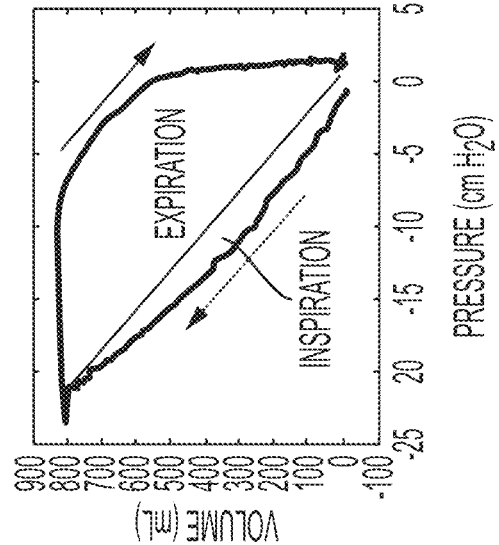
FIG. 27 is a plot showing mean volume-pressure loop for post-extubation (chamber)
Figure 26:
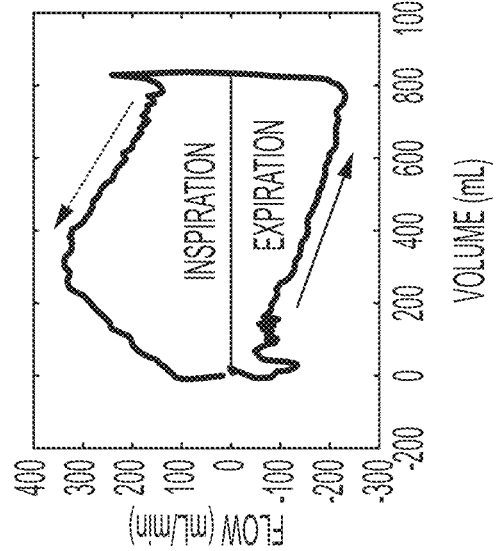
FIG. 26 is a plot showing mean flow-volume loop for post-extubation (trachea)

FIGS. 24 and 25 display mean flow-volume and mean pressure-volume loops, respectively, under positive pressure ventilation (closed chest phase). Pressure and flow were measured at the tracheal port. FIGS. 26 and 27 display similar data under negative pressure ventilation (post-extubation phase), except with pressure measured at the chamber port (flow measured at the tracheal port). FIG. 28 shows mean pressure-volume under negative pressure, but with the pressure measured at the tracheal port. In all subplots of FIGS. 24-28, volume was computed from flow measured at the tracheal port. Lines and labels in FIGS. 24-28 indicate inspiration and expiration portions of the loops, and arrows indicate direction along the loops. Table 2, below, summarizes mean maximum tracheal pressures (positive pressure), mean minimum chamber pressures (negative pressure), and maximum lung volumes (based on trachea pressure) for each tested lung as well as pooled values for all lungs. Table 2 provides a summary of means and standard deviations of maximum inspiratory volume, trachea pressure, and leak rate from positive pressure (closed chest) and negative pressure (post-extubation) ventilation from each tested lung. Minimum chamber pressures from negative pressure ventilation are also provided in Table 2. Mean+/− standard deviation in Table 2 is from all cycles within a given testing phase. Means and pooled standards deviation from all nine animals are provided in the rightmost column of Table 2.

TABLE 2

| | | Lung01 | Lung02 | Lung03 | Lung04 | Lung05 |
|---|---|---|---|---|---|---|
| Positive Pressure Ventilation | Max Inspiratory Volume (ml) | 694 +/− 190 | 477 +/− 222 | 522 +/− 62.4 | 767 +/− 29.7 | 781 +/− 32.2 |
| | Max Trachea Pressure (cm H20) | 40.3 +/− 2.15 | 37.8 +/− 0.243 | 41.2 +/− 0.328 | 40.6 +/− 0.705 | 39.8 +/− 0.104 |
| | Leak Rate (ml/min) | 80.1 +/− 8.59 | 73.4 +/− 3.20 | 109 +/− 25.1 | 19.1 +/− 7.52 | 153 +/− 9.69 |
| Negative Pressure Ventilation | Max Inspiratory Volume (ml) | 718 +/− 291 | 617 +/− 347 | 605 +/− 163 | 812 +/− 114 | 495 +/− 219 |
| | Max Trachea Pressure (cm H20) | 2.40 +/− 0.241 | 13.1 +/− 1.32 | 1.26 +/− 0.419 | 7.32 +/− 1.38 | 9.40 +/− 0.536 |
| | Min Chamber Pressure (cm H20) | −19.4 +/− 2.94 | −18.4 +/− 4.10 | −14.1 +/− 2.54 | −18.4 +/− 4.26 | −9.02 +/− 0.81 |
| | Leak Rate (ml/min) | 324 +/− 55.0 | 205 +/− 8.55 | 1180 +/− 107 | 95.8 +/− 6.31 | 350 +/− 23.8 |

| | | Lung06 | Lung07 | Lung08 | Lung09 | Mean +/− Pooled Std. Dev. |
|---|---|---|---|---|---|---|
| Positive Pressure Ventilation | Max Inspiratory Volume (ml) | 477 +/− 41.2 | 587 +/− 46.5 | 516 +/− 48.7 | 548 +/− 37.2 | 597 +/− 105 |
| | Max Trachea Pressure (cm H20) | 36.3 +/− 0.219 | 30.4 +/− 0.238 | 41.0 +/− 0.190 | 48.9 +/− 0.555 | 39.6 +/− 0.799 |

TABLE 2-continued

| | | | | | | |
|---|---|---|---|---|---|---|
| | Leak Rate (ml/min) | 133 +/− 9.55 | 77.1 +/− 6.30 | 45.7 +/− 6.41 | 116 +/− 7.07 | 89.5 +/− 11.0 |
| Negative Pressure Ventilation | Max Inspiratory Volume (ml) | 511 +/− 68.0 | 681 +/− 94.6 | 708 +/− 79.6 | 633 +/− 77.7 | 642 +/− 188 |
| | Max Trachea Pressure (cm H20) | 8.66 +/− 0.352 | 1.08 +/− 0.968 | 7.28 +/− 0.809 | 16.1 +/− 0.625 | 7.41 +/− 0.835 |
| | Min Chamber Pressure (cm H20) | −26.4 +/− 1.16 | −15.4 +/− 3.89 | −19.9 +/− 0.90 | −18.8 +/− 2.42 | −17.8 +/− 2.86 |
| | Leak Rate (ml/min) | 1100 +/− 30.1 | 72.2 +/− 31.7 | 210 +/− 45.8 | 360 +/− 31.5 | 433 +/− 47.2 |

Figure 29:
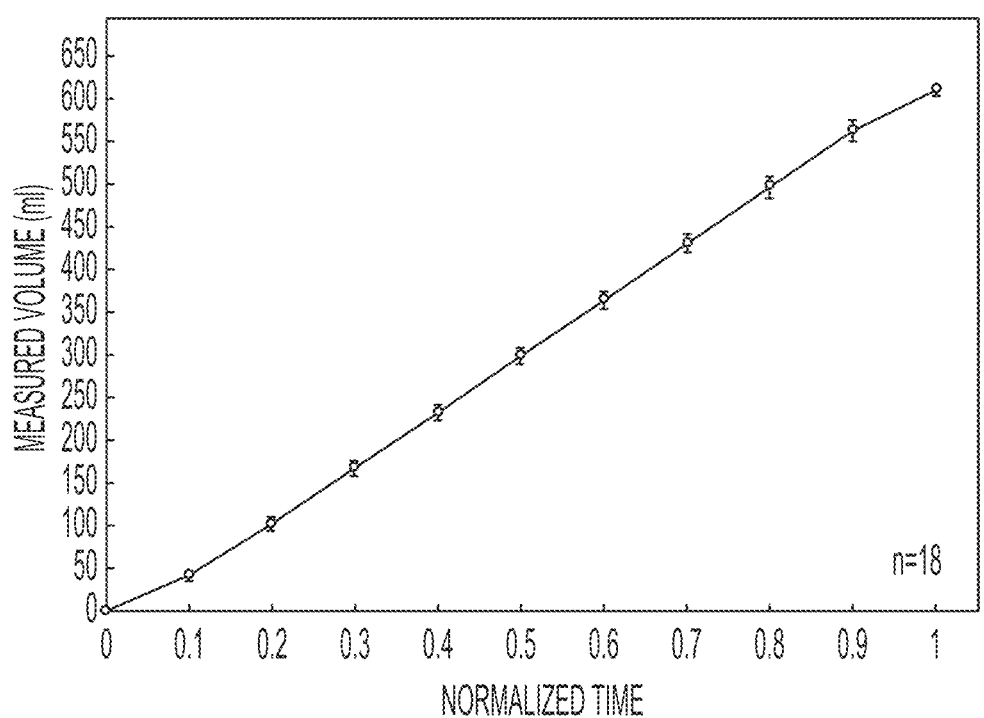
FIG. 29 is a graph showing mean measured volume vs. normalized time.
Figure 30:
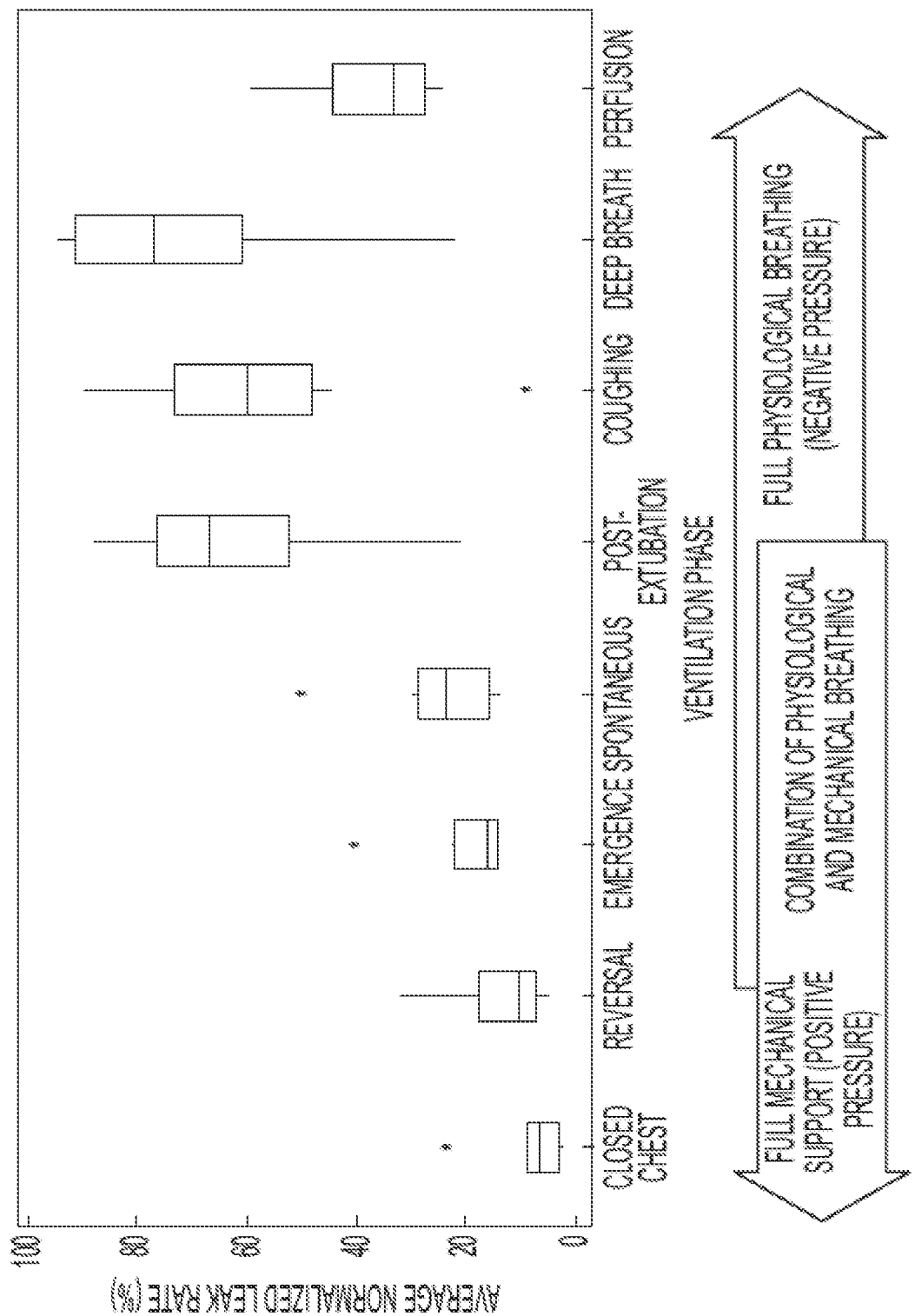
FIG. 30 is a plot showing normalized average leak rates.

Mean+/− standard deviation of leak volume (ml) versus normalized time for the eighteen syringe validation trials is shown in FIG. 29. Volumes were accurate to within ±6.5 ml or ~1% at each normalized time. Measured volumes deviated minimally from the actual injected volumes through most of the test, with the greatest discrepancies (+/−6.5% of injected volume) observed at the start and end of the test. Air leak data for each ventilation phase and from each lung set was collected and plotted as bar plots of average normalized leak rate (%) over the course of the testing phases (FIG. 30). Interquartile range box in FIG. 30 shows 50% of the data, with the whiskers denoting the upper and lower 25% of the distribution. Asterisks in FIG. 30 indicate data outside of the upper and lower quartiles. Note that as negative pressure ventilation is introduced (reversal, emergence, spontaneous), leak rate increases above that at the closed chest phase (full positive pressure). Upon switching to full negative pressure (post-extubation), the average leak rate substantially increases and is maintained during coughing, deep breath, and perfusion phases. Closed chest showed an average normalized leak rate (7.66%+/−6.46%), with leak rate gradually increasing through reversal, emergence, and spontaneous (negative pressure with full mechanical support) phases. A sharp increase was observed between spontaneous (24.7%+/−11.1%) and post-extubation phases (63.3%+/−20.0%), which marked the onset of full negative-only pressure ventilation. Coughing and deep breathing phases had minimal impact on leak rate. Perfusion the lungs (averaged for n=3 specimens), decreased the leak rate (36.8%+/−12.2%) from post-extubation slightly, but it was still larger than the positive pressure phases.

Figure 31:
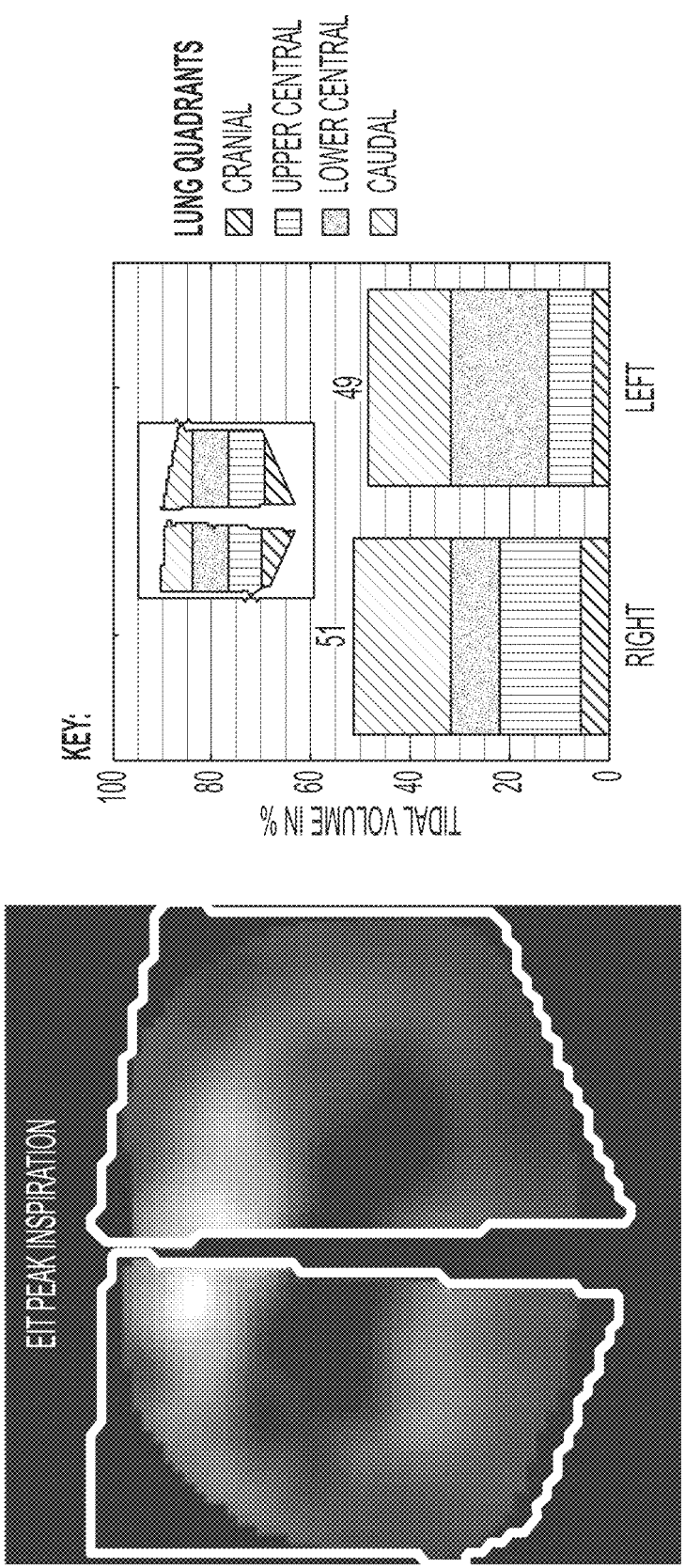
FIG. 31 is an image showing electrical impedance tomography (EIT) peak inspiration.
Figure 32:
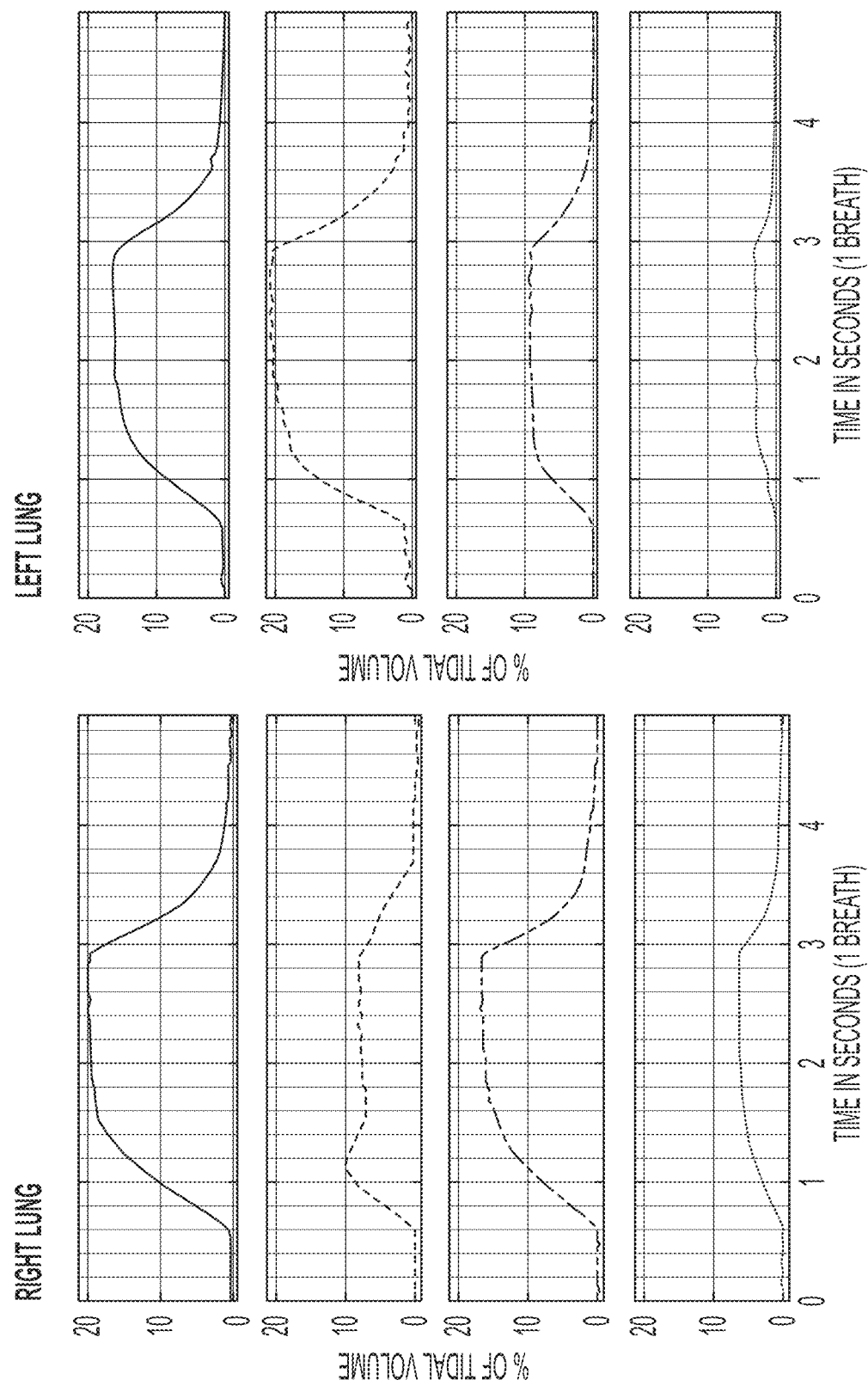
FIG. 32 are graphs showing tidal volume percentage between right and left lungs.
Figure 33:
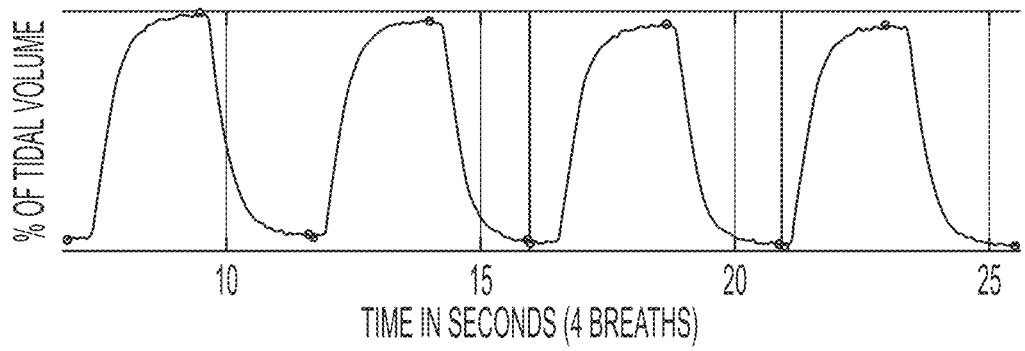
FIG. 33 is a graph showing total impedance change vs. time.

A representative analysis of EIT data is shown in FIGS. 31-33. FIG. 31 shows EIT image from peak inspiration of a single cycle, with rough outline of the lungs shown in white, while FIG. 32 shows distribution of tidal volume percentage between right and left lungs with colored bars representing tidal volume percentage from quadrants of each lung. Peak impedance (FIG. 31) within the EIT ring fit that of the lung set outline. Right/left lung set distribution was nearly evenly split (FIG. 32) with further distinction into quadrants showing similar tidal volume distributions in the cranial and caudal regions. Differences in the central quadrants were evident but may have resulted from the presence of the accessory lobe (right lung) in the lower central quadrant. Individual quadrant impedance versus time (FIG. 32) and total impedance change versus time (FIG. 33) displayed regular patterns that followed the system's prescribed volume versus time waveform. In FIG. 32, tidal volume percentage vs. time is plotted for each quadrant from both sides; note the similar distribution in tidal volume percentage between right and left lungs in the caudal and cranial quadrants. The difference between distributions in the central quadrants could be due to the location of the heart (lowering impedance) and the presence of the accessory lobe. In FIG. 33, tidal volume for the entire lung set vs. time is presented for four cycles.

Figure 34:
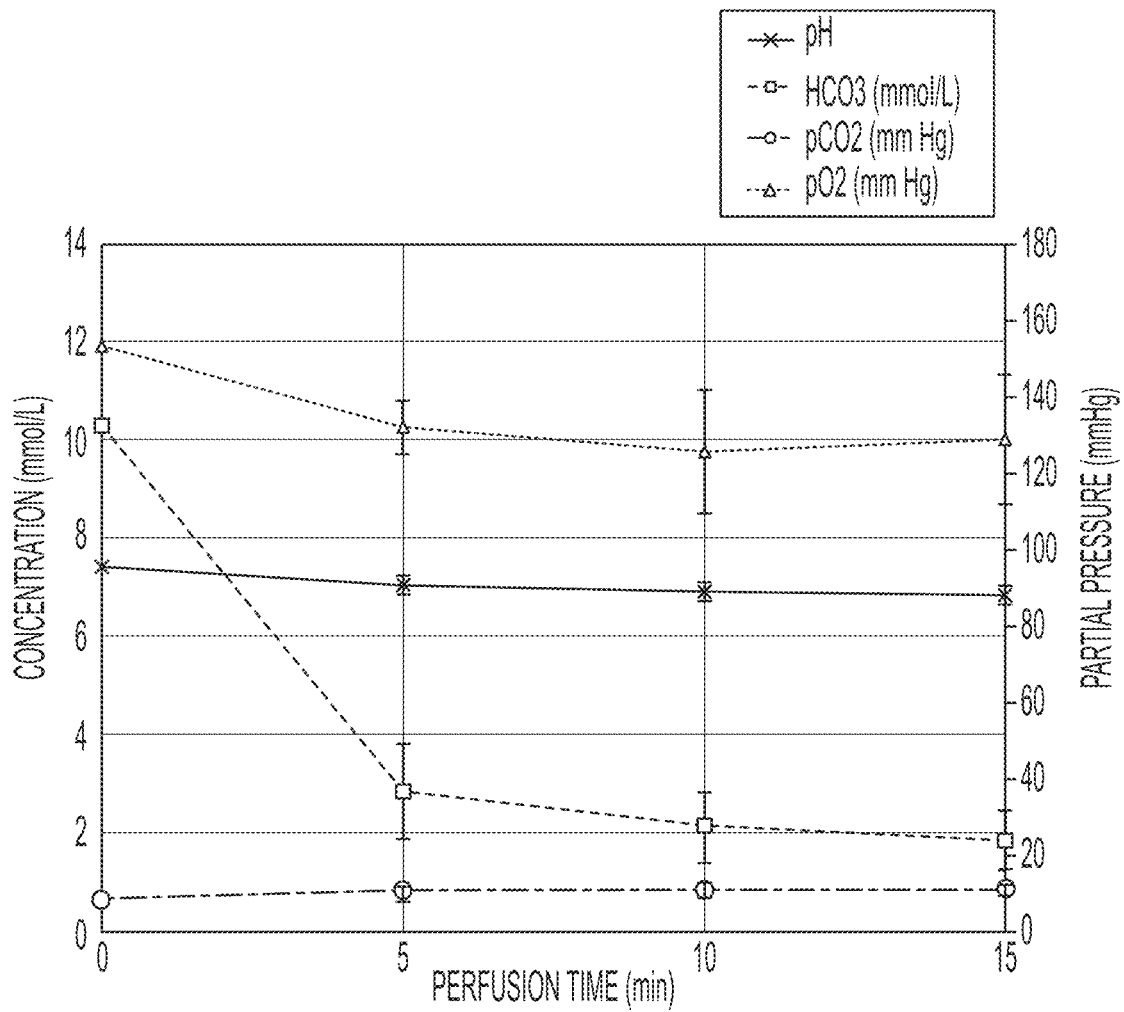
FIG. 34 is a graph showing perfusate gas analysis vs. perfusion time.

Summary data from the perfusate analysis are presented below in Table 3. Baseline (0 min) data in Table 3 is from single sample analysis of perfusate before circulating in lungs. Perfusate samples were taken from LA pressure transducer port. BE in Table 3 denotes base excess, iCa denotes ionized calcium, and sO2 represents oxygen saturation. A total of six lung sets were perfused, though not all electrolytes/blood gasses were measured by the i-stat device at each time interval; therefore, the number of samples used to compute the mean and standard deviation are presented as well. Mean+/−standard deviation of pH, $pCO_2$, $pO_2$, and $HCO_3$ are shown in FIG. 34. Throughout ventilation, $pO_2$ was maintained at 125-132 mm Hg under room air. $PCO_2$ increased throughout perfusion from 7.4 to 10.4 mm Hg while pH dropped from 7.40 to 6.83. Glucose decreased from 92 mg/dl (baseline) to 65-68 mg/dl during ventilation. Bicarbonate ion concentration ($HCO_3$) dropped from 10.3 mmol/L (baseline) to 2.8 mmol/L and then steadily decreased to 1.8 mmol/L. Sodium and potassium ions did not substantially change from baseline. During initial perfusion, pH, $pO_2$, and $pCO_2$ dropped—the drop in pH is suggestive of acidosis, with the drop in $HCO_3$ suggestive of a metabolic cause. Glucose data (shown in Table 3) supports metabolic acidosis. Through continued perfusion, $pO_2$ stabilized and remained above 93% saturation.

TABLE 3

| | | 5 min | | | 10 min | | | 15 min | | |
|---|---|---|---|---|---|---|---|---|---|---|
| | 0 min | Mean | Std. Dev. | N | Mean | Std. Dev. | N | Mean | Std. Dev. | N |
| pH | 7.40 | 7.04 | 0.193 | 4 | 6.90 | 0.183 | 5 | 6.83 | 0.165 | 6 |
| pCO2 (mmHg) | 7.4 | 9.9 | 1.3 | 4 | 10.4 | 1.5 | 5 | 10.4 | 0.95 | 6 |
| PO2 (mmHg) | 153 | 132 | 7.02 | 4 | 125 | 16.5 | 5 | 129 | 17.4 | 6 |
| BE (mmol/L) | −9 | <−30 | NA | 4 | <−30 | NA | 5 | <−30 | NA | 6 |
| HCO3 (mmol/L) | 10.3 | 2.8 | 0.98 | 4 | 2.1 | 0.74 | 5 | 1.8 | 0.62 | 6 |

TABLE 3-continued

|  | 0 min | 5 min | | | 10 min | | | 15 min | | |
| --- | --- | --- | --- | --- | --- | --- | --- | --- | --- | --- |
|  |  | Mean | Std. Dev. | N | Mean | Std. Dev. | N | Mean | Std. Dev. | N |
| sO2 (%) | 100 | 97 | 1.6 | 4 | 94 | 3.3 | 5 | 94 | 3.5 | 6 |
| Na (mmol/L) | 145 | 144 | 6.03 | 4 | 145 | 5.69 | 5 | 148 | 7.26 | 6 |
| K (mmol/L) | 7.7 | 7.8 | 0.42 | 4 | 7.9 | 0.35 | 5 | 7.6 | 0.37 | 6 |
| iCa (mmol/L) | <0.25 | <0.25 | NA | 4 | <0.25 | NA | 5 | <0.25 | NA | 6 |
| Glucose (mg/dl) | 92 | 65 | 8.2 | 3 | 67 | 1.5 | 3 | 68 | 5.6 | 4 |

As shown in the summary table, tracheal and chamber pressures were consistent among the n=9 tested lungs as evidenced by the small standard deviations. Maximum inspiratory volumes were somewhat more varied, both within a lung and across lungs. Since these tests were run under a pressure-limited volume control mode, inspiration may have stopped prior to the volume set point if the pressure limit was reached (40 cm $H_2O$ pressure); therefore, some variations in volume could have resulted. Additionally, the presence of leak (especially under negative pressure) could have influenced maximum inspiratory volumes, and normal animal-animal variations could have contributed to the volume differences between individual lungs. Overall, considering the sources of variation, the standard deviations in lung volumes were low. Minimum chamber pressure (negative pressure) and leak rate were consistent within each lung and among all tested lungs.

In the air leak quantification system validation, a slight underestimation/overestimation was observed within the first and last ~4 seconds of the test, likely due to the selected gain constant in the ultrasonic sensor by which the removal pump was activated (to return the fluid level back the set point). Overall, the discrepancies from anticipated values were exceptionally small, which built confidence in the leak collection and quantification system.

The above results demonstrate the capacity of the model to mimic various breathing modalities in intra- and post-operative settings and in the ability to capture and quantify air leaks. The model represents a step beyond previous models of negative pressure ventilation of isolated lungs by employing a submerged lung model with controlled volumetric expansion of the chamber to expand the lungs as opposed to application of a pressure gradient to induce a volume change. By using volume change to induce negative pressure, the model provides control over both respiratory rate and tidal volume simultaneously, allowing for highly controlled physiologic breathing mechanics.

Mean flow-volume (QV) loops were produced that exhibited the same general progression of ventilation conditions as in clinical volume-controlled mechanical ventilation and patient spirometry curves. Like typical QV loops under mechanical ventilation, a sharp increase in flow followed by a plateau was observed during inspiration. A sharp decrease in flow with a gradual return to zero marked expiration. Inspiration rates were slightly smaller than expiration rates, which is typical under normal airway resistance. In the QV loops under negative pressure ventilation, a sharp increase in flow at the beginning of inhalation followed by a gradual tapering as peak tidal volume was achieved, similar to normal breathing spirometry curves. Some flow restriction was observed in the ventilation system, as shown by a slight blunting of the QV spirometry curves. This was likely created by the tracheal cannulation, pneumotach, solenoid, and tubing; similarly, intubated patients also face flow restrictions not dissimilar to that shown in the model.

The pressure-volume (PV) loops under mechanical ventilation had similar features to clinical patient loops, with a broad increase in pressure towards peak volume. Note in these experiments, a PEEP of ~5-7 cm $H_2O$ was maintained, and the volume control ventilation mode (set to 800 ml volume) had a pressure limit of 40 cm $H_2O$. Upon expiration, the curve exhibited minimal change in volume with pressure decrease, which implied an increased in compliance. The lung defect may have contributed to the changes in the shape of the expiration curve. Since each of the lungs leaked, inspired air volume may have preferentially exited the leak site during the onset of expiration until sufficiently lower trachea pressure drew the remaining volume out of the trachea.

Under negative pressure ventilation, the trachea PV loop showed the tidal volume change with minimal change in pressure, as expected with naturally breathing lungs with a small CPAP applied. Negative pressure PV loops which approximated intrapleural pressure with chamber pressure displayed a similar pattern as in positive pressure ventilation, with a steady increase in volume with pressure change (negative in this case) upon inspiration and a more rapid decrease in volume with pressure increasing back to zero. Again, increased compliance and the presence of air leaks could have contributed to the shape of the PV curve.

Intentionally introducing a defect in the lungs to induce an air leak and monitoring leak through various simulated intra- and post-operative breathing phases gave rise to surprising leak rate results. Marginal increases in leak rate were observed as the ventilation mode changed from full mechanical support (positive pressure) towards spontaneous breathing (intermittent positive pressure with full negative pressure ventilation). Interestingly, a sharp rise in leak rate was evident in the post-extubation phase (full negative pressure breathing). This transition between positive and negative pressure ventilation appears to represent a critical factor in determining the magnitude of the leak rate. Further stressing of the lungs (cough, deep breath) did not have a significant impact on leak rate. The underlying mechanism driving this apparent marked difference in leak rate with pressure modality will likely be an important topic of further exploration in future tests with this ex vivo lung system. One hypothesis as to the observed difference is that the pressure modalities are fundamentally different in how they interact with tissue. In the case of positive pressure, air is being forced into the large airways, overcoming increasing airway resistance to reach the alveoli. When alveolar pressure exceeds that of the pleural pressure (and overcomes tissue elasticity), the lungs inflate. Under negative pressure, the entire pleural surface of the lung is being acted upon, with the pressure pulling the lung open. As pleural pressure drops below alveolar pressure, the pressure gradient acts to pull the lungs open. Since such forces directly influence tissue deformation, existing lung damage/holes may be more susceptible to stretching open under negative versus positive pressure. As observed in the PV curves in this study, a much larger pressure gradient was generated during positive pressure ventilation (approximately 40 cm $H_2O$) compared to negative pressure (approximately −18 cm $H_2O$) with comparable tidal volumes, suggesting that negative pressure ventilation is more efficient at inflating lung than positive pressure ventilation. Additionally, the mass effect of surrounding lung segments that may compress the leak during positive pressure ventilation may be reduced or removed during negative ventilation, thereby worsening the leak.

The use of EIT in this work helped enabled the evaluation of gas distribution within the lungs during ventilation. Although other technologies exist such as xenon-gas contrast enhanced CT and hyperpolarized xenon or helium gas enhanced MRI scans, the difficulty of implementing these systems within the model was impractical in this work. EIT proved successful in identifying ventilation of the entire lung as well as comparison of ventilation within the sides and regions (quadrants of each side) of the lung. Overall, the data suggests that the lungs ventilated equally between sides, with high impedances (indicative of ventilation) observed in the region near the leak site. Impedance curves followed that of the tracheal pressure curves. Areas of low impedance (notably the center of the ring) matched with the approximate location of the heart (which would have a lower impedance than air).

Results of the perfusate analysis are consistent with published data on glucose metabolism, indicating organ viability. The observed mild acidosis and electrolyte changes match that of tissue perfusion and ischemia reperfusion injury in lungs with cold ischemia time of twenty-four hours and longer. Measured LA (pulmonary venous) oxygen and carbon dioxide partial pressures are representative of tissue ventilation and perfusion and are similar to prior data on prolonged isolated lung culture—important observations to drive towards functional lungs in the model.

Testing was limited to an acute, 80-minute time frame; as PALs often manifest 1-2 days after surgery, there may be critical changes in leak rates that were not observed in the current testing. Finally, although the use of a saline bath was essential to capture and quantify leaks, the addition of a hydrostatic pressure on the lungs may have induced non-physiologic deformations. This risk was mitigated by limiting leaks to the ventral surface of the lungs which resided near the top of the chamber, greatly minimizing the hydrostatic head at the leak site and therefore variation between test samples.

Future work with the model can include a focus on replicating leaks from lung resection procedures associated with tissue handling as well as with stapling devices to evaluate resulting leaks under the different pressure modalities. Additionally, the potential to use transplant-rejected human tissue with pathological states clinically representative of patients would greatly deepen understanding of the science around leak etiology, specifically as it applies to the surgical arena. Finally, lengthening the testing phase to better approach post-operative periods where PALs manifest (up to two days), may add novel insights into how leaks change over clinically-relevant time periods.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A medical air leak modeling system, comprising:
   a first liquid-tight and air-tight chamber configured to have a liquid therein and to have a lung immersed in the liquid in the first chamber;
   a second liquid-tight and air-tight chamber;
   a tube connecting the first chamber with the second chamber to allow liquid to circulate between the first and second chambers;
   a first pump configured to circulate fluid between the first chamber to the second chamber;
   a sensor configured to sense a liquid fill level in the second chamber; and
   a control unit operatively coupled to the sensor, the control unit being configured to, in response to the sensor sensing a threshold amount of change in the fill level, activate a second pump to cause the second pump to pump liquid from the first chamber to the second chamber.

2. The system of claim 1, wherein the fluid includes liquid and air, the second pump is a peristaltic pump, and the control unit is configured to use an amount of rotation of the peristaltic pump in pumping the fluid from the first chamber to the second chamber in determining an amount of air moved from the first chamber to the second chamber by the first pump.

3. The system of claim 1, further comprising a balloon configured to be immersed in the liquid in the first chamber.

4. The system of claim 1, further comprising a pressure mechanism located outside of the first chamber and configured to inflate and deflate the lung immersed in the liquid in the first chamber.

5. The system of claim 4, wherein the pressure mechanism includes a ventilator configured to provide oscillating positive pressure to the lung immersed in the liquid in the first chamber.

6. The system of claim 4, wherein the pressure mechanism includes a piston configured to provide negative pressure to the lung immersed in the liquid in the first chamber.

7. The system of claim 4, further comprising a balloon configured to be immersed in the liquid in the first chamber, the balloon being configured to deflate from a default inflated state in response to the lung being inflated.

8. The system of claim 1, wherein a top wall of the first chamber has a dome shape to allow for collection of air between the top wall and a top of the liquid in the first chamber.

9. The system of claim 8, further comprising a port at a top of the dome shape, and a second tube connected to the port and to the second chamber;
   wherein the dome shape is the only domed portion of the top wall, and the first pump is configured to circulate the fluid through the second tube.

10. The system of claim 8, wherein the dome shape includes a plurality of dome shapes in the top wall, each of the dome shapes having a port at a top thereof, and the first pump is configured circulate the fluid through a selected one of the ports.

11. The system of claim 1, further comprising a trachea port in a wall of the first chamber, the trachea port being configured to operatively couple to the lung to allow liquid to flow out of the lung and out of the first chamber through the trachea port.

12. The system of claim 11, wherein a second tube extends from the trachea port outside of the first chamber;
a pinch valve is located along the second tube; and
the pinch valve is configured to selectively move between an open position, in which the pinch valve does not obstruct flow through the second tube, and a closed position, in which the pinch valve obstructs flow through the second tube.

13. The system of claim 1, further comprising a heater operatively coupled to the first chamber and configured to heat the lung immersed in the liquid in the first chamber.

14. The system of claim 1, wherein the control unit is configured to, in response to the sensor sensing the fill level being substantially equal to a predetermined fill level, deactivate the second pump to stop the second pump to end air removal from the second chamber.

15. The system of claim 1, wherein walls of the first chamber are transparent to allow visualization of the lung in the first chamber from outside the first chamber.

16. A medical air leak modeling system, comprising:
a liquid-tight and air-tight chamber, wherein:
the chamber is configured to have a liquid therein with a lung immersed in the liquid adjacent a bottom wall of the chamber,
a top wall of the chamber includes a domed portion that allows for collection of air between the top wall and a top of the liquid in the first chamber, and
a top of the domed portion has a port therein configured to allow the collected air to exit therethrough; and
a pressure mechanism located outside of the chamber and configured to inflate and deflate the lung immersed in the liquid in the chamber, wherein, in response to the inflation and deflation, a leak present in the lung releases air from the lung into liquid and then into the domed portion.

17. The system of claim 16, further comprising a balloon configured to be immersed in the liquid in the chamber, the balloon being configured to deflate from a default inflated state in response to the lung being inflated.

18. The system of claim 16, wherein the pressure mechanism includes at least one of:
a ventilator configured to provide oscillating positive pressure to the lung immersed in the liquid in the chamber; and
a piston configured to provide negative pressure to the lung immersed in the liquid in the first chamber.

19. The system of claim 16, further comprising a second liquid-tight and air-tight chamber in fluid communication with the first chamber;
a first pump configured to pump fluid through the port and into the second chamber;
a sensor configured to sense a liquid fill level of liquid in the second chamber; and
a control unit operatively coupled to the sensor, the control unit being configured to, in response to the sensor sensing a threshold amount of change in the fill level, activate a second pump to cause the second pump to pump liquid from the first chamber to the second chamber.

20. A medical air leak modeling method, comprising:
circulating fluid between a first liquid-tight and air-tight chamber and a second liquid-tight and air-tight chamber, the first chamber having a lung therein that is immersed in liquid;
sensing with a sensor a liquid fill level in the second chamber;
in response to the sensor sensing a threshold amount of change in the fill level, activating a peristaltic pump to cause the pump to pump liquid from the first chamber to the second chamber; and
using an amount of rotation of the peristaltic pump in pumping the air from the first chamber to the second chamber to determine an amount of air that leaked from the lung during the circulation of fluid.

* * * * *